United States Patent
Bell et al.

(10) Patent No.: US 8,476,320 B2
(45) Date of Patent: *Jul. 2, 2013

(54) FORMULATIONS FOR PARENTERAL ADMINISTRATION OF AMINO-SUBSTITUTED (E)-2, 6-DIALKOXYSTYRYL 4-SUBSTITUTED BENZYLSULFONES

(75) Inventors: Stanley C. Bell, Narberth, PA (US); Janice W Bell, legal representative, Narberth, PA (US); Manoj Maniar, Fremont, CA (US)

(73) Assignee: Onconova Therapeutics, Inc, Newtown, PA (US)

( * ) Notice: Subject to any disclaimer, the term of this patent is extended or adjusted under 35 U.S.C. 154(b) by 659 days.

This patent is subject to a terminal disclaimer.

(21) Appl. No.: 12/523,305

(22) PCT Filed: Jan. 16, 2008

(86) PCT No.: PCT/US2008/000523
§ 371 (c)(1), (2), (4) Date: Oct. 13, 2009

(87) PCT Pub. No.: WO2008/088803
PCT Pub. Date: Jul. 24, 2008

(65) Prior Publication Data
US 2010/0152096 A1    Jun. 17, 2010

Related U.S. Application Data

(60) Provisional application No. 60/880,376, filed on Jan. 16, 2007.

(51) Int. Cl.
*A61K 31/10* (2006.01)

(52) U.S. Cl.
USPC .......................................................... 514/710

(58) Field of Classification Search
None
See application file for complete search history.

(56) References Cited

FOREIGN PATENT DOCUMENTS
WO       03/072062 A2 *   9/2003
WO    WO 2006/010152       1/2006

OTHER PUBLICATIONS

Dash et al. AAPS Annual Meeting and Exposition, Nov. 2005, Abstract attached.*

Strickley, R.G. Pharmaceutical Research, Feb. 2004, vol. 21, pp. 201-230.*
Gumireddy et al. Cancer Cell, Mar. 2005, vol. 7, pp. 275-286.*
International Search Report for PCT/US08/00523, mailed on Aug. 1, 2008.*

* cited by examiner

*Primary Examiner* — James D Anderson
(74) *Attorney, Agent, or Firm* — Houri Khalilian; Law Offices of Khalilian Sira, LLC

(57) ABSTRACT

Formulations are provided for parenteral administration of (amino substituted (e)-2,6-dialkoxystyryl 4-substituted benzylsulfones and the sodium and potassium salts thereof for the prevention and/or treatment of conditions mediated by abnormal cell proliferation.

Composition for parenteral administration are provided which comprise an effective amount of a compound of formula I

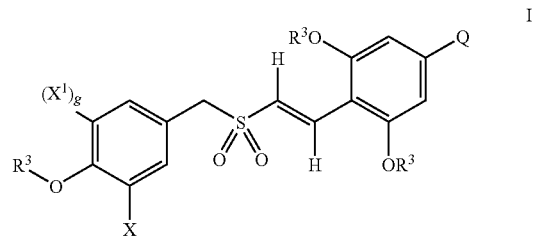

or a compound of formula IIa

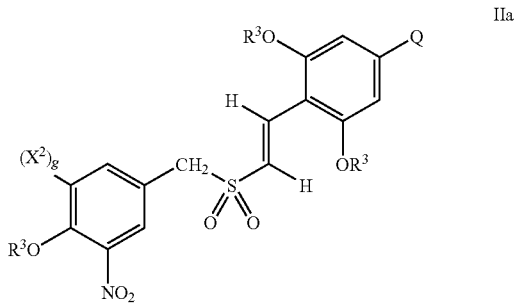

and at least about 50% by weight of at least one water soluble polymer selected from the group consisting essentially of polyethylene glycol (PEG), poly-oxyethylene, poly-oxyethylene-poly-oxypropylene copolymers, polyglycerol, polyvinylalcohol, polyvinylpyrrolidone (PVP), polyvinylpyridine N-oxide, copolymer of vinylpyridine N-oxide and vinylpyridine.

12 Claims, 2 Drawing Sheets

Figure 7-8: The Synthesis of ON 01910.Na

FORMULATIONS FOR PARENTERAL ADMINISTRATION OF AMINO-SUBSTITUTED (E)-2,6-DIALKOXYSTYRYL 4-SUBSTITUTED BENZYLSULFONES

FIELD OF THE INVENTION

The invention relates to compositions for parenteral delivery of certain kinase inhibitors and methods for the treatment of cancer and proliferative disorders related thereto.

BACKGROUND OF THE INVENTION

Protein tyrosine kinases are enzymes which catalyze a well defined chemical reaction: the phosphorylation of a tyrosine residue (Hunter et al., Annu Rev Biochem 54:897 (1985)). Receptor tyrosine kinases in particular are attractive targets for drug design since blockers for the substrate domain of these kinases is likely to yield an effective and selective antiproliferative agent. The potential use of protein tyrosine kinase blockers as antiproliferative agents was recognized as early as 1981, when quercetin was suggested as a PTK blocker (Graziani et al., Eur. J. Biochem. 135:583-589 (1983)).

The best understood MAPK pathway involves extracellular signal-regulated kinases which constitute the Ras/Raf/MEK/ERK kinase cascade (Boudewijn et al., Trends Biochem. Sci. 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

Formulations are needed to stabilize new anticancer chemotherapeutic agents which target receptor tyrosine kinases and which arrest the Ras/Raf/MEK/ERK kinase cascade. Oncoproteins in general, and signal transducing proteins in particular, are likely to be more selective targets for chemotherapy because they represent a subclass of proteins whose activities are essential for cell proliferation, and because their activities are greatly amplified in proliferative diseases. However, the new anticancer chemotherapeutic agents are generally hydrophobic and unstable and therefore are unusually difficult to formulate for storage and efficacy upon parenteral administration.

Anticancer formulations are needed to enable efficacious delivery of certain kinase inhibitors and corollary selection in the killing of proliferating cells such as tumor cells.

SUMMARY OF THE INVENTION

The invention is directed to formulations for parenteral administration of amino-substituted (e)-2,6-dialkoxystyryl 4-substituted benzylsulfones and the sodium and potassium salts thereof for the prevention and/or treatment of conditions mediated by abnormal cell proliferation.

Composition for parenteral administration are provided which comprise an effective amount of a compound of formula I

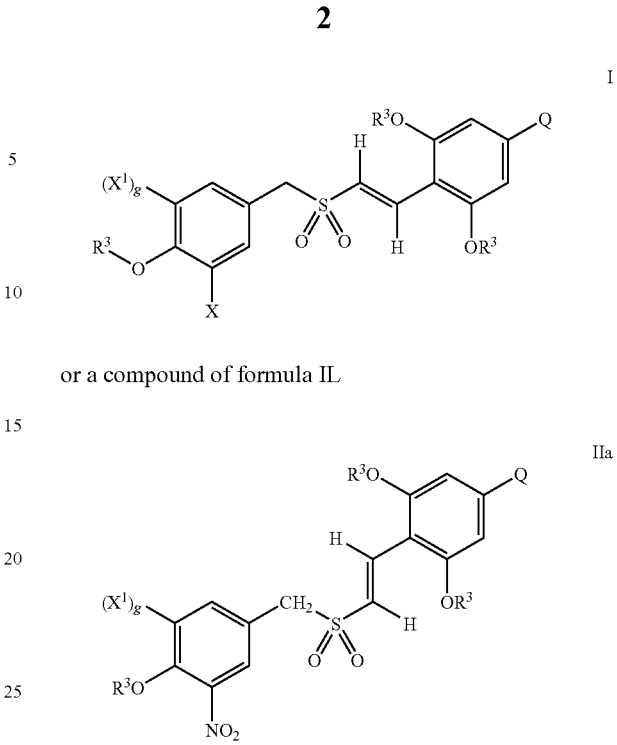

or a compound of formula II, and at least about 25% by weight of at least one water soluble polymer selected from the group consisting essentially of polyethylene glycol (PEG), poly-oxyethylene, poly-oxyethylene-poly-oxypropylene copolymers, polyglycerol, polyvinylalcohol, polyvinylpyrrolidone (PVP), polyvinylpyridine N-oxide, copolymer of vinylpyridine N-oxide and vinylpyridine.

DETAILED DESCRIPTION OF THE INVENTION

Figure 1:
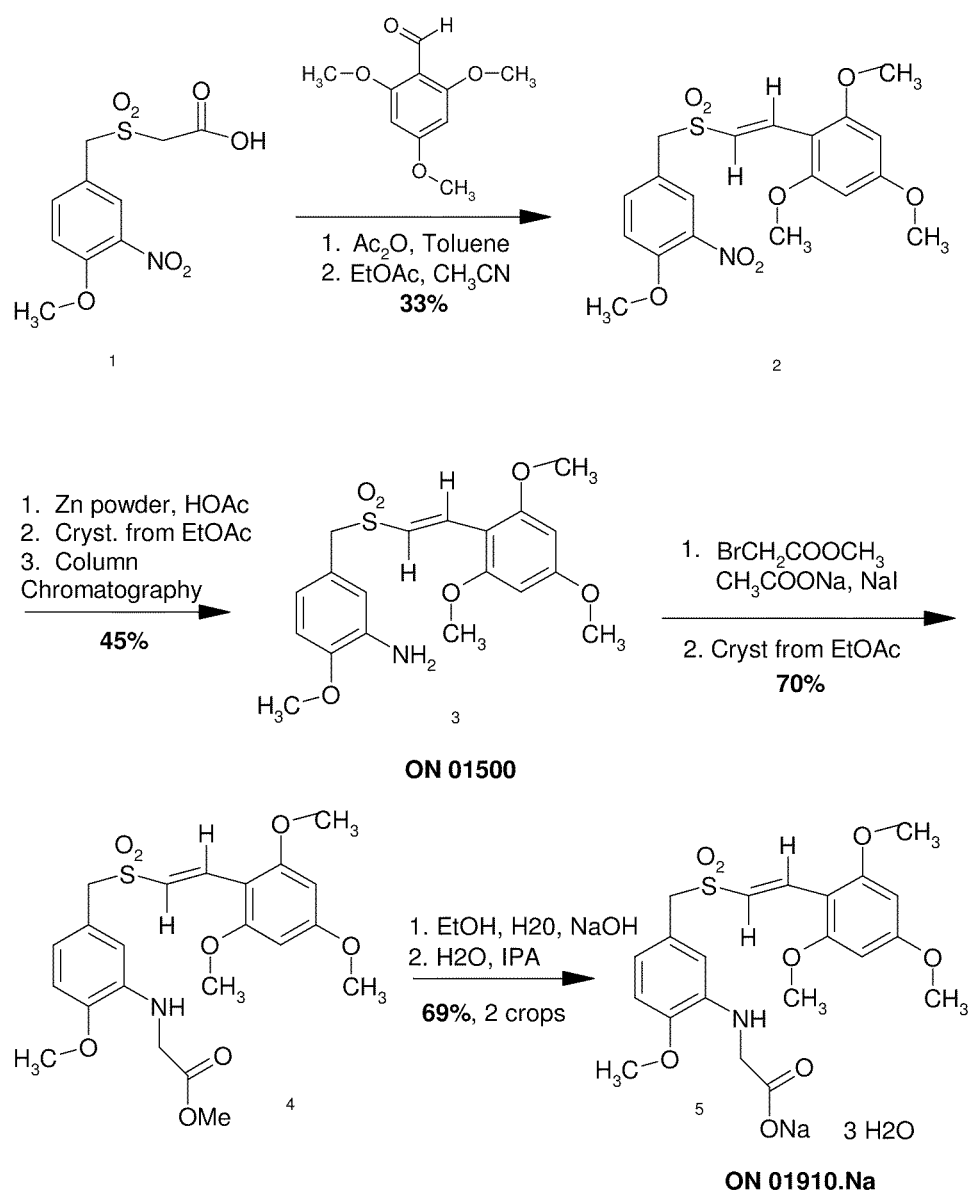
FIG. 1 displays a flowchart outlining a method of synthesis of the sodium salt of (E)-2,4,6-trimethoxystyryl-3-carboxymethylamino-4-methoxybenzylsulfone (ON 01910.Na).

Unless defined otherwise, all technical and scientific terms used herein have the same meaning as is commonly understood by one of skill in the art to which this invention belongs. All publications and patents referred to herein, including U.S. Pat. No. 6,486,210, entitled Substituted Styryl Benzylsulfones for Treating Proliferative Disorders, are incorporated by reference in their entirety.

Compounds for which compositions and formulations of the present invention are intended, i.e., (amino substituted (e)-2,6-dialkoxystyryl 4-substituted benzylsulfones (herein referred to as "compounds"), as the Applicants have previously disclosed in the above-referenced copending applications, are valuable therapeutic compounds for the prevention and/or treatment of pathophysiological disorders related to mammalian cell growth. The compounds, however, are generally hydrophobic. These compounds are accordingly unusually difficult to formulate for storage and efficacy upon parenteral administration. Parenteral administration includes, for example, intravenous, intramuscular, intraarterial, intraperitoneal, intranasal, rectal, intravaginal, intravesical (e.g., to the bladder), intradermal, topical, sublingual or subcutaneous administration. Moreover, improved properties are provided upon stabilization of the compounds in formulations as described herein.

I. Structural Genus

A. Compounds for Use in Compositions of the Present Invention Include Amino-Substituted (e)-2,6-dialkoxystyryl 4-Substituted Benzylsulfones of Formula I

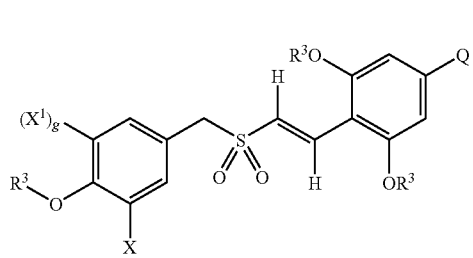

I wherein:

X is selected from the group consisting of (i) and (ii) below:

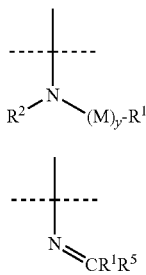

$X^1$ is selected from the group consisting of (i), (ii) and (iii) below:

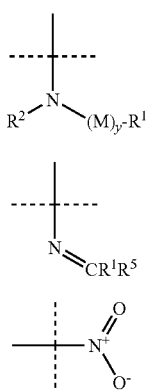

wherein $X^1$ is optionally protected with one or more chemical protecting groups;

g is 0 or 1;

each M is a bivalent connecting group independently selected from the group consisting of —$(C_1$-$C_6)$alkylene, —$(CH_2)_a$—V—$(CH_2)_b$, —$(CH_2)_d$—W—$(CH_2)_e$— and —Z—;

each y is independently selected from the group consisting of 0 and 1;

each V is independently selected from the group consisting of arylene, heteroarylene, —C(=O)—, —C(=S)—, —S(=O)—, —SO$_2$—, —C(=O)O—; —C(=O)$(C_1$-$C_6)$perfluoroalkylene-, —C(=O)NR$^4$—, —C(=S)NR$^4$— and —SO$_2$NR$^4$—;

each W is independently selected from the group consisting of —NR$^4$—, —O— and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

—Z— is

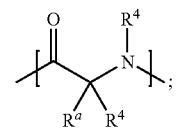

wherein the absolute stereochemistry of —Z— is D or L or a mixture of D and L;

each $R^a$ is independently selected from the group consisting of —H, —$(C_1$-$C_6)$alkyl, —$(CH_2)_3$—NH—C(NH$_2$)(=NH), —CH$_2$C(=O)NH$_2$, —CH$_2$COOH, —CH$_2$SH, —$(CH_2)_2$C(=O)—NH$_2$, —$(CH_2)_2$COOH, —CH$_2$-(2-imidazolyl), —CH(CH$_3$)—CH$_2$—CH$_3$, —CH$_2$CH(CH$_3$)$_2$, —$(CH_2)_4$—NH$_2$, —$(CH_2)_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and includes compounds wherein $R^a$ and $R^1$ combine to form a 5-, 6- or 7-membered heterocyclic ring;

each $R^1$ is independently selected from the group consisting of —H, unsubstituted aryl, substituted aryl, substituted heterocyclic, unsubstituted heterocyclic, —CO$_2$R$^5$, —C(=O)NR$^4$$_2$, —CR$^4$R$^6$R$^7$, —C(=NH)—NR$^4$$_2$, —$(C_1$-$C_6)$perfluoroalkyl, —CF$_2$Cl, —P(=O)(OR$^4$)$_2$, —OP(=O)(OR$^4$)$_2$ and a monovalent peptidyl moiety with a molecular weight of less than 1000; provided that when y is 0 and $R^1$ is —CO$_2$R$^5$, $R^5$ is not —H;

each $R^2$ is independently selected from the group consisting of —H, —$(C_1$-$C_6)$alkyl, and aryl$(C_1$-$C_3)$alkyl, wherein —$R^2$ and -(M)$_y$-$R^1$ may optionally be linked covalently to form a 5-, 6- or 7-membered substituted or unsubstituted heterocycle;

each $R^3$ is independently selected from —$(C_1$-$C_6)$alkyl;

each $R^4$ is independently selected from the group consisting of —H, and —$(C_1$-$C_6)$alkyl;

wherein:

when $R^4$ and $R^1$ are bonded to the same nitrogen atom, $R^1$ and $R^4$ may combine to form a heterocycle; and when two $R^4$ groups are geminally bonded to the same nitrogen, the two $R^4$ groups may combine to form a heterocycle;

each $R^5$ is independently selected from the group consisting of —H, —$(C_1$-$C_6)$alkyl and —$(C_1$-$C_6)$acyl;

each $R^6$ is independently selected from the group consisting of —H, —$(C_1$-$C_6)$alkyl, —CO$_2$R$^5$, —C(=O)R$^7$, —OR$^5$, —OC(=O)(CH$_2$)$_2$CO$_2$R$^5$, —SR$^4$, guanidino, —NR$^4$$_2$, —N⁺R⁴₃, —N⁺(CH₂CH₂OH)₃, phenyl, substituted phenyl, heterocyclic, substituted heterocyclic and halogen;

each R⁷ is independently selected from the group consisting of —H, —Rᵃ, halogen, —(C₁-C₆)alkyl, —NR⁴₂ and heterocycles containing two nitrogen atoms; and Q is selected from the group consisting of —H, —(C₁-C₆)alkoxy, halogen, —(C₁-C₆)alkyl and —NR⁴₂;

wherein the substituents for the substituted aryl and substituted heterocyclic groups comprising or included within R¹, Rᵃ, R², R⁶ and R⁷, are independently selected from the group consisting of halogen, (C₁-C₆)alkyl, (C₁-C₆)alkoxy, —NO₂, —C≡, —CO₂R⁵, —C(=O)O(C₁-C₃)alkyl, —OR⁵, —(C₂-C₆)—OH, phosphonato, —NR⁴₂, —NHC(=O)(C₁-C₆)alkyl, sulfamyl, —OC(=O)(C₁-C₃)alkyl, —O(C₂-C₆)—N((C₁-C₆)alkyl)₂ and —CF₃;

provided (1) when R¹ is a monovalent peptidyl moiety of molecular weight less than 1000 and V is —C(=O)—, —C(=S)—, —S(=O)— or —SO₂—, and b is 0; then said peptidyl moiety is coupled to M through the amino terminus of the peptidyl moiety or through a sidechain amino group to form an amide, thioamide, sulfinamide or sulfonamide respectively;

(2) when R¹ is a monovalent peptidyl moiety of molecular weight less than 1000 and V is —C(=O)NR³—, —SO₂NR³—, or —NR⁴—, and b is 0, then said peptidyl moiety is coupled to M through the carboxy terminus of the peptidyl moiety or through a sidechain carboxyl group to form an imide, sulfonimide, or carboxamide respectively; and (3) when R¹ is a monovalent peptidyl moiety of molecular weight less than 1000 and W is —S— or —O—, and d is 0, then said peptidyl moiety is coupled to M through the carboxy terminus of the peptidyl moiety or through a sidechain carboxyl group to form a carbothioic acid ester or the carboxylic ester respectively;

or a salt of such a compound.

According to one sub-embodiment thereof, compounds of formula I are provided, wherein:

each V is independently selected from the group consisting of —C(=O)—, —C(=S)—, —S(=O)—, —SO₂—; —C(=O)NR⁴—, —C(=S)NR⁴— and —SO₂NR⁴—;

—Z— is

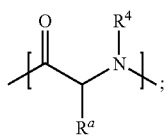

wherein the absolute stereochemistry of —Z— is either D or L each Rᵃ is independently selected from the group consisting of —H, —CH₃, —(CH₂)₃—NH—C(NH₂)(=NH), —CH₂C(=O)NH₂, —CH₂COOH, —CH₂SH, —(CH₂)₂C(=O)—NH₂, —(CH₂)₂COOH, —CH₂-(2-imidazolyl), —CH(CH₃)—CH₂—CH₃, —CH₂CH(CH₃)₂, —(CH₂)₄—NH₂, —(CH₂)₂—S—CH₃, phenyl, CH₂-phenyl, —CH₂—OH, —CH(OH)—CH₃, —CH₂-(3-indolyl), —CH₂-(4-hydroxyphenyl), —CH(CH₃)₂ and —CH₂—CH₃; and includes compounds wherein Rᵃ and R¹ combine to form a 5-, 6- or 7-membered heterocyclic ring;

each R¹ is independently selected from the group consisting of —H, unsubstituted aryl, substituted aryl, substituted heterocyclic, unsubstituted heterocyclic, —CO₂R⁵, —C(=O)NR⁴₂, —CHR⁶R⁷, —C(=NH)—NR⁴₂, and a monovalent peptidyl moiety with a molecular weight of less than 1000; provided that when y is 0 and R¹ is —CO₂R⁵, R⁵ is not —H;

each R⁶ is independently selected from the group consisting of —H, —(C₁-C₆)alkyl, —CO₂R⁵, —C(=O)R⁷, —OH, —SR⁴, —(C₁-C₃)alkoxy, —(C₁-C₃)alkylthio, guanidino, —NR⁴₂, phenyl, substituted phenyl, heterocyclic, substituted heterocyclic and halogen; and each R⁷ is independently selected from the group consisting of —H, halogen, —(C₁-C₆)alkyl, —NR⁴₂ and heterocycles containing two nitrogen atoms;

wherein the substituents for the substituted aryl and substituted heterocyclic groups comprising or included within R', Rᵃ, R², R⁶ and R⁷, are independently selected from the group consisting of halogen, (C₁-C₆)alkyl, (C₁-C₆)alkoxy, —NO₂, —C≡N, —CO₂R⁵, —C(=O)O(C₁-C₃)alkyl, —OH, —(C₂-C₆)—OH, phosphonato, —NR⁴₂, —NHC(=O)(C₁-C₆)alkyl, sulfamyl, —OC(=O)(C₁-C₃)alkyl, —O(C₂-C₆)—N((C₁-C₆)alkyl)₂ and —CF₃.

According to a preferred sub-embodiment, there are provided compounds of formula I, wherein each V is independently selected from the group consisting of

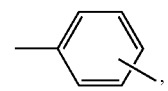

—C(=O)—, —C(=S)—, —S(=O)—, —SO₂—, —C(=O)O—; —C(=O)NR⁴—, —C(=S)NR⁴— and —SO₂NR⁴—.

According to a more preferred sub-embodiment thereof, there are provided compounds of formula I, wherein each V is independently selected from the group consisting of

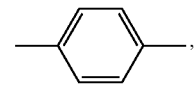

—C(=O)—, —C(=S)—, —S(=O)—, —SO₂—, —C(=O)O—; —C(=O)NR⁴—, —C(=S)NR⁴— and —SO₂NR⁴—.

According to another sub-embodiment thereof, there are provided compounds of formula I, wherein Z has an L absolute configuration.

Preferred compounds of formula I, include for example, the following compounds and salts thereof:

(E)-2,4,6-trimethoxystyryl-3-[4-(4-methylpiperazin-1-yl]benzamido)-4-methoxy-benzylsulfone;

(E)-2,4,6-trimethoxystyryl-3-(acetoxyacetamido)-4-methoxy-benzylsulfone;

(E)-2,4,6-trimethoxystyryl-3-(triethylammoniumacetamido)-4-methoxybenzyl-sulfone;

(E)-2,4,6-trimethoxystyryl-3-[tri-(2-hydroxyethylammonium)acetamido]-4-methoxy-benzylsulfone;

(E)-2,4,6-trimethoxystyryl-3-(2-methyl-2-hydroxypropionamido)-4-methoxybenzyl-sulfone;

(E)-2,4,6-trimethoxystyryl-3-(2-methyl-2-acetoxypropionamido)-4-methoxybenzyl-sulfone;

(E)-2,4,6-trimethoxystyryl-3-(2-acetoxypropionamido)-4-methoxybenzylsulfone;

(E)-2,4,6-trimethoxystyryl-3-(trifluoroacetamido)-4-methoxybenzylsulfone;

(E)-2,4,6-trimethoxystyryl-3-(trifluoromethanesulfonamido)-4-methoxybenzyl-sulfone;
(E)-2,4,6-trimethoxystyryl-3-[3-(3-carboxypropanoyloxy)acetamido]-4-methoxy-benzylsulfone;
(E)-2,4,6-trimethoxystyryl-3-(phosphonatoacetamido)-4-methoxybenzylsulfone, disodium salt;
(E)-2,4,6-trimethoxystyryl-3-(methylcarbamoyl)-4-methoxybenzylsulfone;
(E)-2,4,6-trimethoxystyryl-3-(2,2-difluoromalonamido)-4-methoxybenzylsulfone;
(E)-2,4,6-trimethoxystyryl-3-(pentafluoropropionamido)-4-methoxybenzylsulfone;
(E)-2,4,6-trimethoxystyryl-3-(methyl-2,2-difluoromalonamido-4-methoxybenzyl-sulfone;
(E)-2,4,6-trimethoxystyryl-3-(2,2-difluoromalonamido)-4-methoxybenzylsulfone;
(E)-2,4,6-trimethoxystyryl-3-(dimethylamino-α,α-difluoroacetamido)-4-methoxy-benzylsulfone; and
(E)-2,4,6-trimethoxystyryl-3-(2,2,3,3,tetrafluorosuccinamido)-4-methoxybenzyl-sulfone.

According to a first embodiment of formula I,
X is

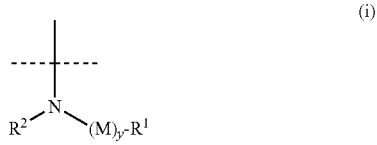

and y is 0; and $R^2$ is —H.

According to a sub-embodiment, there are provided compounds of the formula III, below:

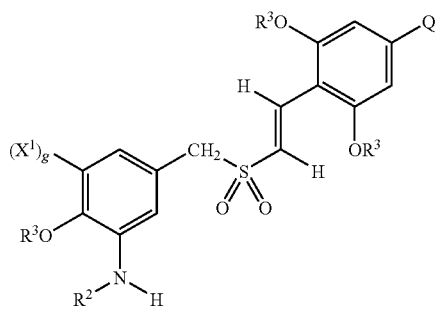

wherein:
g is 0 or 1;
each $R^2$ is independently selected from the group consisting of —H, —$(C_1-C_6)$alkyl, and aryl$(C_1-C_3)$alkyl, wherein —$R^2$ and -$(M)_y$-$R^1$ may optionally be linked covalently to form a 5-, 6- or 7-membered substituted or unsubstituted heterocycle;
each $R^3$ is independently selected from —$(C_1-C_6)$alkyl;
each $R^4$ is independently selected from the group consisting of —H, and —$(C_1-C_6)$alkyl;
Q is selected from the group consisting of —H, —$(C_1-C_6)$alkoxy, halogen, —$(C_1-C_6)$alkyl and —$NR^4_2$; and
$X^1$ is selected from the group consisting of (i), (ii) and (iii) below:

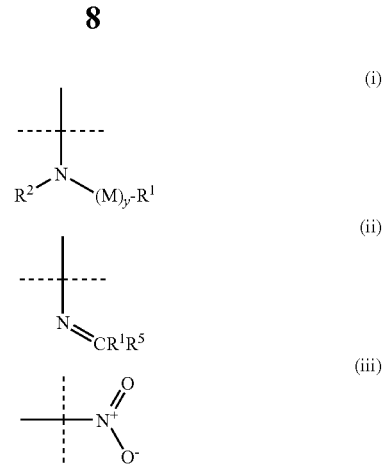

wherein $X^1$ is optionally protected with one or more chemical protecting groups;

Suitable protecting groups will be stable to reactions designed to derivatize the 3-amino group of formula III. Subsequently, said protecting groups are optionally removed to regenerate the $X^1$.

In another sub-embodiment, there are provided compounds of the formula IIIa, below:

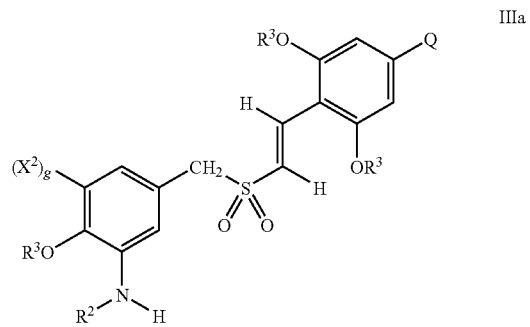

wherein $X^2$ is selected from the group consisting of —$NO_2$ and —$NH_2$, wherein said —$NH_2$ is optionally protected with a chemical protecting group.

A strategy for synthesizing compounds of formula I involves derivatization of an primary or secondary amino group at the 3-position of formula IIIa. Such derivatizations of the 3-amino group include for example reactions to form carboxamides, sulfonamides alkyl amines, nitrogen-containing heterocycles, imines, guanidines, ureas, amidines, and amino ketones.

The intermediate of formula IIIa also incorporates a nitro group or a protected amino group at the 5-position. In the synthetic strategy, this 5-substituent serves as a second, latent amino group. The use of this protecting group strategy allows for differential derivatization of these two amino groups, i.e., the 3-amino group of formula IIIa and the moiety at the 5-position which is inert to the conditions of the derivatization of the 3-amino group. Hence, the synthetic route involves first derivatizing the 3-amino group, followed by conversion of the 5-substituent to an amino group via either (a) deprotection, if $X^2$ is a protected amine, or (b) chemical reduction if $X^2$ is a nitro group. Hence, from a retrosynthetic viewpoint, the synthetic route allows for differential derivatization of two amino groups, one at the 5-position which is protected (either with a chemical protecting group, or by being in a nitro oxidation state) and thereby inert to the conditions of the derivatization of the 3-amino group. Suitable chemical protecting groups for the 5-position protected amine, include for example, benzyl, 2,4-dimethoxy-benzyl and benzyloxycarbonyl (CBZ). In a similar manner, when $X^2$ is —$NO_2$, the 3-amino group may be derivatized in the aforesaid manner. Subsequently the —$NO_2$ group may optionally be chemically reduced to the corresponding 5-amino group via a variety of procedures known to those skilled in the art.

Subsequently, the 5-amino group, generated by either reduction of a 5-nitro group or by removing a protecting group from a protected 5-amino compound, is optionally derivatized. Derivatization of the 5-amino group may be the same or different from the derivatization of the 3-amino group.

According to a sub-embodiment of the aforesaid compounds of formula IIIa, compounds are provided wherein Q is —($C_1$-$C_6$)alkoxy.

According to another sub-embodiment of formula IIIa, Q is —$OCH_3$. According to a further sub-embodiment of formula IIIa, $R^3$ is —$CH_3$. One such compound is (E)-2,4,6-trimethoxystyryl-4-methoxy-3-amino-benzylsulfone.

According to a second embodiment of formula I,
X is

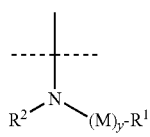

(i)

and $R^2$ is —H, y is 0; and $R^1$ is selected from the group consisting of unsubstituted aryl, substituted aryl, substituted heterocyclic, unsubstituted heterocyclic, —$CO_2R^3$, —C(=O)$NR^4_2$, —$CHR^6R^7$, —C(=NH)—$NR^4_2$ and a monovalent peptidyl moiety with a molecular weight of less than 1000.

According to a third embodiment of formula I,
X is

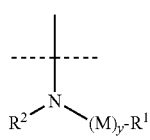

(i)

and y is 1; M is —($CH_2$)$_a$—V—($CH_2$)$_b$—; and V is —C(=O)—.

According to a sub-embodiment thereof, compounds of the formula IV, below and salts thereof, are provided:

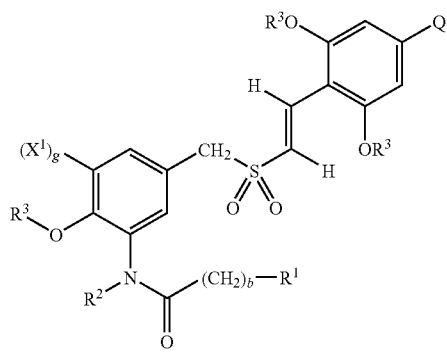

IV

Preferred compounds of formula IV, include for example, the following compounds and salts thereof:
(E)-2,4,6-trimethoxystyryl-3-(carboxyacetamido)-4-methoxybenzylsulfone;
(E)-2,4,6-trimethoxystyryl-3-(3,5-dinitrobenzamido)-4-methoxybenzyl-sulfone;
(E)-2,4,6-trimethoxystyryl-3-(3,5-diaminobenzamido)-4-methoxybenzyl-sulfone;
(E)-2,4,6-trimethoxystyryl-3-(chloroacetamido)-4-methoxybenzylsulfone;
(E)-2,4,6-trimethoxystyryl-3-[(4-methylpiperazinyl)acetamido]-4-methoxy-benzylsulfone;
(E)-2,4,6-trimethoxystyryl-3-(benzamido)-4-methoxybenzylsulfone;
(E)-2,4,6-trimethoxystyryl-3-(4-nitrobenzamido)-4-methoxybenzylsulfone;
(E)-2,4,6-trimethoxystyryl-3-(4-aminobenzamido)-4-methoxybenzylsulfone;
(E)-2,4,6-trimethoxystyryl-3-(acetamido)-4-methoxybenzylsulfone;
(E)-2,4,6-trimethoxystyryl-3-(dimethylaminoacetamido)-4-methoxybenzyl-sulfone;
(E)-2,4,6-trimethoxystyryl-3-(hydroxyacetamido)-4-methoxy-benzylsulfone;
(E)-2,4,6-trimethoxystyryl-3-(2-hydroxypropionamido)-4-methoxy-benzylsulfone
(E)-2,4,6-trimethoxystyryl-3-(pyridinium-1-yl)acetamido-4-methoxybenzyl-sulfone;
(E)-2,4,6-trimethoxystyryl-3-(ethylmalonamido)-4-methoxy-benzylsulfone;
(E)-2,4,6-trimethoxystyryl-3-(glutaramido)-4-methoxybenzylsulfone
(E)-2,4,6-trimethoxystyryl-3-(methylsuccinamido)-4-methoxybenzylsulfone;
(E)-2,4,6-trimethoxystyryl-3-(succinamido)-4-methoxybenzylsulfone;
(E)-2,4,6-trimethoxystyryl-3-(3-chlorosuccinamido)-4-methoxybenzyl-sulfone; and
(E)-2,4,6-trimethoxystyryl-3-(aminoacetamido)-4-methoxybenzylsulfone;
or a salt of such a compound.

According to a fourth embodiment of formula I; X is

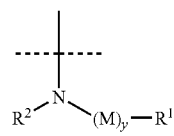

(i)

and y is 1; and M is —Z—.

According to a sub-embodiment thereof, compounds of formula V and salts thereof, are provided:

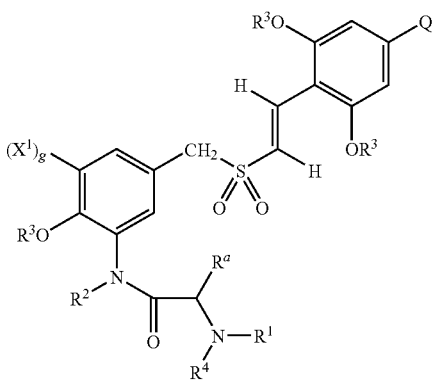

V wherein:

each $R^a$ is independently selected from the group consisting of —H, —CH$_3$, —(CH$_2$)$_3$—NH—C(NH$_2$)(=NH), —CH$_2$C(=O)NH$_2$, —CH$_2$COOH, —CH$_2$SH, —(CH$_2$)$_2$C(=O)—NH$_2$, —(CH$_2$)$_2$COOH, —CH$_2$-(2-imidazolyl), —CH(CH$_3$)—CH$_2$—CH$_3$, —CH$_2$CH(CH$_3$)$_2$, —(CH$_2$)$_4$—NH$_2$, —(CH$_2$)$_2$—S—CH$_3$, phenyl, CH$_2$-phenyl, —CH$_2$—OH, —CH(OH)—CH$_3$, —CH$_2$-(3-indolyl), —CH$_2$-(4-hydroxyphenyl), —CH(CH$_3$)$_2$ and —CH$_2$—CH$_3$; and includes compounds wherein $R^a$ and $R^1$ combine to form a 5-, 6- or 7-membered heterocyclic ring;

Heterocyclic rings formed by the combination of $R^a$ and $R^1$ include for example: pyrrolidine, hydroxy pyrrolidine, piperidine, homopiperidine and thiazolidine.

Preferred compounds of formula V, include for example the following compounds and salts thereof:

(E)-2,4,6-trimethoxystyryl-3-amino-4-methoxybenzylsulfone-L-lysineamide;

(E)-2,4,6-trimethoxystyryl-3-amino-4-methoxybenzylsulfone-L-serineamide; and (E)-2,4,6-trimethoxystyryl-3-amino-4-methoxybenzylsulfone-D-serineamide.

According to a fifth embodiment of formula I:
X is

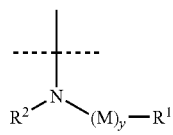

(i)

and y is 1; M is —(CH$_2$)$_a$—V—(CH$_2$)$_b$—; and V is —SO$_2$—.

According to a sub-embodiment thereof compounds of formula VI and salts thereof, are provided:

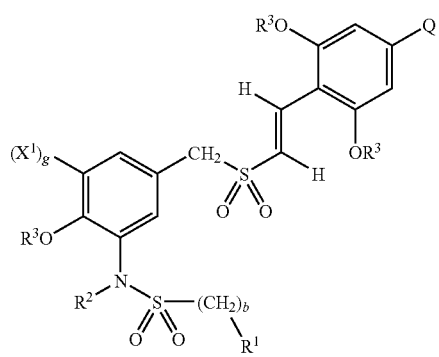

VI

Compounds of formula VI, include for example the following compounds and salts thereof:

(E)-2,4,6-trimethoxystyryl-3-carboxymethylsulfamyl-4-methoxy-benzylsulfone;

(E)-2,4,6-trimethoxystyryl-3-(4-methoxybenzenesulfamyl)-4-methoxy-benzylsulfone;

(E)-2,4,6-trimethoxystyryl-3-(2,4-dinitrobenzenesulfamyl)-4-methoxy-benzylsulfone; and (E)-2,4,6-trimethoxystyryl-3-(2,4-diaminobenzenesulfamyl)-4-methoxy-benzylsulfone.

According to a sixth embodiment of formula I, X is

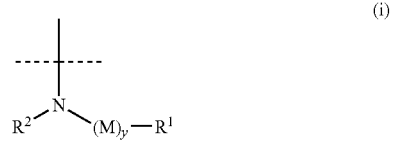

(i)

and y is 0 and $R^1$ is —C(=NH)—NR$^4$$_2$.

According to a sub-embodiment thereof compounds of formula VII, and salts thereof, are provided:

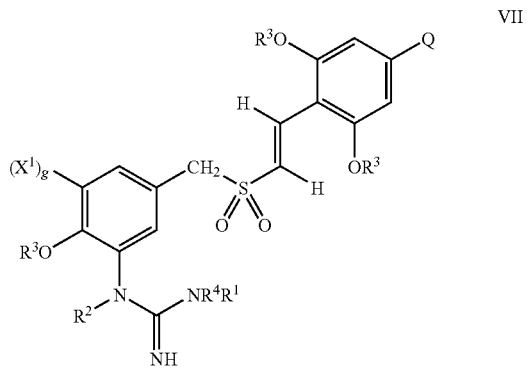

VII

One such compound is (E)-2,4,6-trimethoxystyryl-3-guanidino-4-methoxy-benzylsulfone, or a salt thereof.

According to a seventh embodiment of formula I, X is

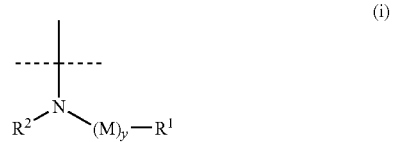

(i)

and y is 1; and M is —(C$_1$-C$_6$)alkylene-.

According to one sub-embodiment thereof, compounds of the formula VIII, and salts thereof, are provided:

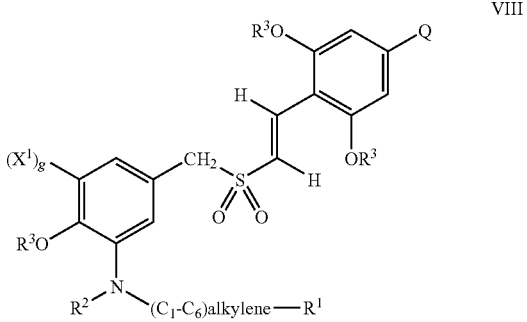

VIII

Exemplary compounds of formula VIII include for example:

(E)-2,4,6-trimethoxystyryl-3-(N-methylamino)-4-methoxy-benzylsulfone;

racemic-(E)-2,4,6-trimethoxystyryl-3-(1-carboxyethyl)amino-4-methoxy-benzylsulfone;

D-(E)-2,4,6-trimethoxystyryl-3-(1-carboxyethyl)amino-4-methoxybenzyl-sulfone;

L-(E)-2,4,6-trimethoxystyryl-3-(1-carboxyethyl)amino-4-methoxybenzyl-sulfone; and
(E)-2,4,6-trimethoxy-styryl-3-(carboxymethylamino)-4-methoxybenzyl-sulfone and salts thereof.

According to an eighth embodiment of compounds of formula I, of the formula IX and salts thereof are provided:

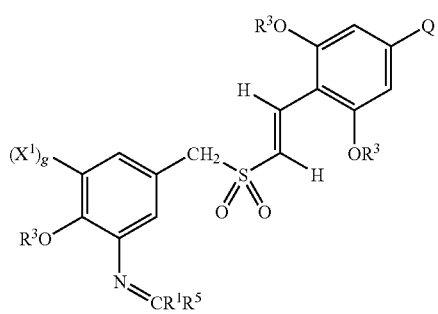

IX

One such compound is (E)-2,4,6-trimethoxystyryl-3-(4-nitrophenylimino)-4-methoxybenzylsulfone or a salt thereof.

According to a ninth embodiment of formula I, X is

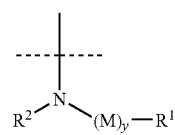

(i)

and y is 1; M is —$(CH_2)_a$—V—$(CH_2)_b$; and V is —C(=O)NR$^4$—.

According to a sub-embodiment thereof, compounds of formula X and salts thereof are provided:

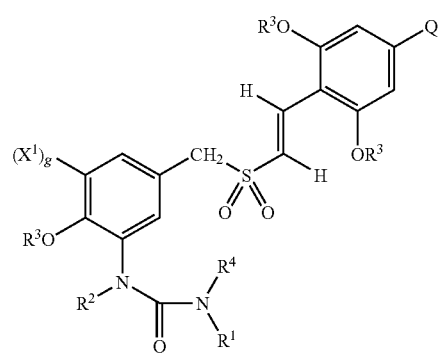

X

An exemplary compound of formula X is (E)-2,4,6-trimethoxystyryl-3-ureido-4-methoxybenzylsulfone, or a salt thereof.

According to a tenth embodiment of formula I, compounds of the formula II and salts thereof are provided:

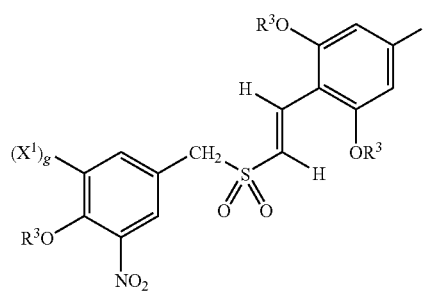

II wherein:
g is 0 or 1;
each R$^3$ is independently selected from —$(C_1$-$C_6)$alkyl;
each R$^4$ is independently selected from the group consisting of —H and —$(C_1$-$C_6)$alkyl;
Q is selected from the group consisting of —H, —$(C_1$-$C_6)$alkoxy, halogen, —$(C_1$-$C_6)$alkyl and —NR$^4{}_2$; and
X$^1$ is selected from the group consisting of (i), (ii) and (iii) below:

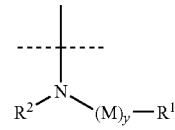

(i)

(ii)

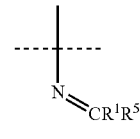

(iii)

wherein X$^1$ is optionally protected with one or more chemical protecting groups;

Suitable protecting groups will be stable to reactions designed to derivatize the 3-amino group of formula III. Subsequently said protecting groups are optionally removed to regenerate the X$^1$.

In another sub-embodiment, thereof, there are provided compounds of the formula IIa, below:

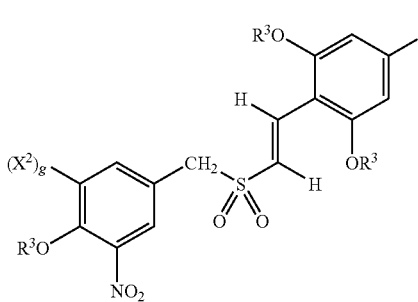

IIa wherein X$^2$ is selected from the group consisting of —NO$_2$ and —NH$_2$, optionally protected with a chemical protecting group.

One such compound of formula IIa is (E)-2,4,6-trimethoxystyryl-4-methoxy-3-nitrobenzylsulfone; or a salt thereof.

According to an eleventh embodiment of formula I, X is

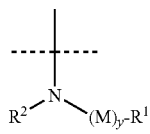

(i)

and y is 0; $R^1$ is —$CHR^6R^7$, $R^6$ is $CO_2R^5$ and $R^7$ is $R^a$;

According to a sub-embodiment thereof, compounds of formula XX and salts thereof are provided:

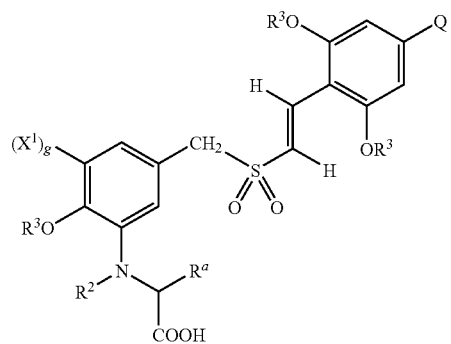

XX

Exemplary compounds of formula XX are (E)-2,4,6-trimethoxystyryl-3-(1-carboxyethyl)amino-4-methoxybenzylsulfone; and (E)-2,4,6-trimethoxystyryl-3-carboxymethylamino-4-methoxybenzylsulfone; or salts thereof.

Preferred compounds are the sodium and potassium salts of (E)-2,4,6-trimethoxystyryl-3-carboxymethylamino-4-methoxybenzylsulfone, particularly the sodium salt.

According to a twelfth embodiment of formula I, X is

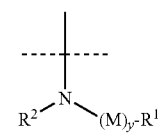

(i)

and y is 1; and M is —(C1-C6)alkylene-.

According to a sub-embodiment thereof, compounds of formula XXI and salts thereof are provided:

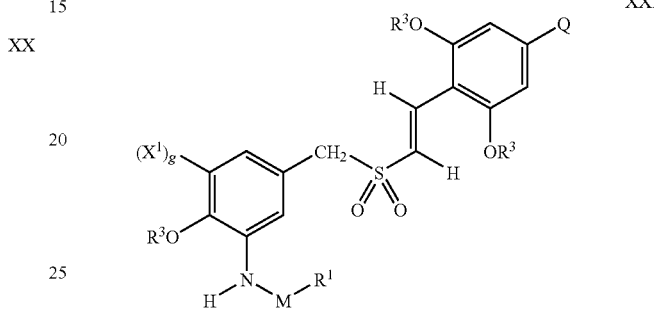

XXI

Exemplary compounds of formula XXI are:
(E)-2,4,6-trimethoxystyryl-3-(3-carboxypropylamino)-4-methoxybenzyl-sulfone;
(E)-2,4,6-trimethoxystyryl-3-(2-carboxyethylamino)-4-methoxybenzyl-sulfone;
or a salt of such a compound.

Example Compounds for Use in Compositions of the Present Invention Include the Following:

TABLE 1

| Compound | Structure | Name |
|---|---|---|
| 1 | (structure shown) | (E)-2,4,6-Trimethoxystyryl-3-(carboxymethylsulfamyl)-4-methoxybenzylsulfone |
| 2 | (structure shown) | (E)-2,4,6-Trimethoxystyryl-3-(carboxyacetamido)-4-methoxybenzylsulfone |

TABLE 1-continued

| Compound | Structure | Name |
|---|---|---|
| 3 | 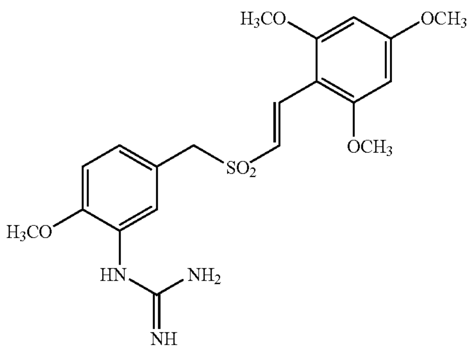 | (E)-2,4,6-Trimethoxystyryl-3-(guanidino)-4-methoxy-benzylsulfone |
| 4 | 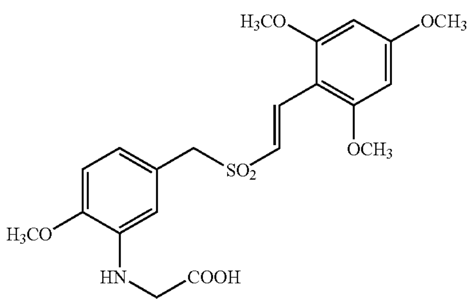 | (E)-2,4,6-Trimethoxystyryl-3-(carboxymethylamino)-4-methoxybenzylsulfone (ON01910) |
| 5 | 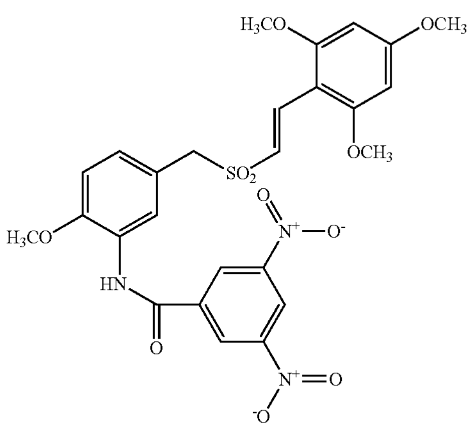 | (E)-2,4,6-trimethoxystyryl-3-(3,5-dinitrobenzamido)-4-methoxybenzylsulfone |
| 6 | 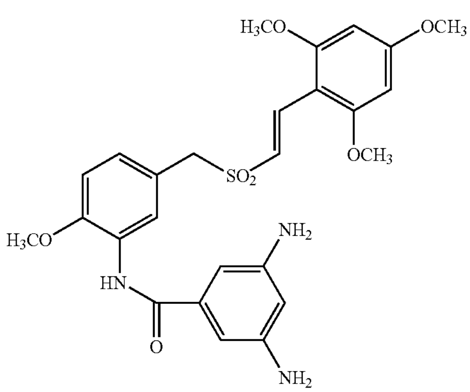 | (E)-2,4,6-trimethoxystyryl-3-(3,5-diamino-benzamido)-4-methoxybenzylsulfone |

TABLE 1-continued
| Compound | Structure | Name |
|---|---|---|
| 7 | 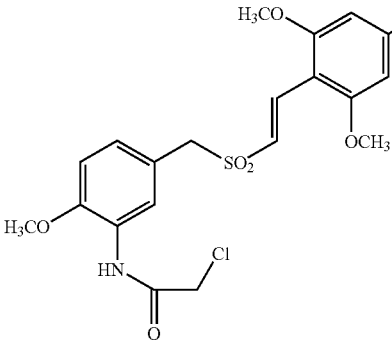 | (E)-2,4,6-Trimethoxystyryl-3-(chloroacetamido)-4-methoxybenzylsulfone |
| 8 | 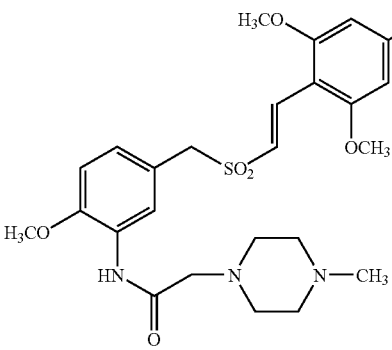 | (E)-2,4,6-Trimethoxystyryl-3-[(4-methylpiperazinyl)-acetamido]-4-methoxy-benzylsulfone |
| 9 | 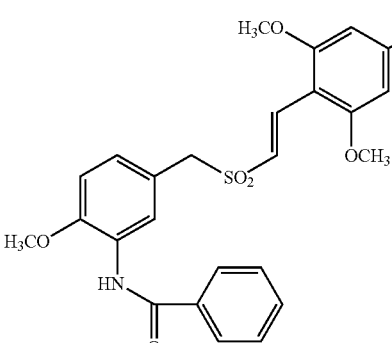 | (E)-2,4,6-Trimethoxystyryl-3-benzamido-4-methoxy-benzylsulfone |
| 10 | 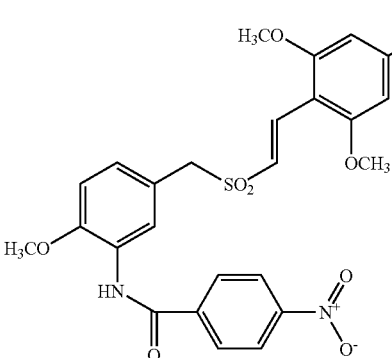 | (E)-2,4,6-Trimethoxystyryl-3-(4-nitrobenzamido)-4-methoxybenzylsulfone |

TABLE 1-continued

| Compound | Structure | Name |
|---|---|---|
| 11 | 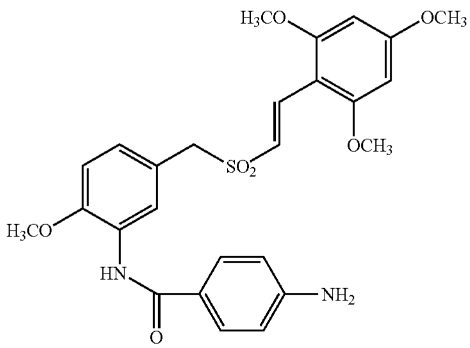 | (E)-2,4,6-Trimethoxystyryl-3-(4-aminobenzamido)-4-methoxybenzylsulfone |
| 12 | 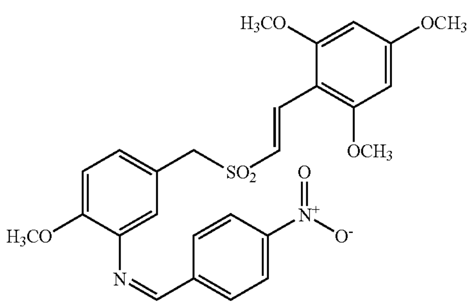 | (E)-2,4,6-Trimethoxystyryl-3-(4-nitrophenylimino)-4-methoxybenzylsulfone |
| 13 | 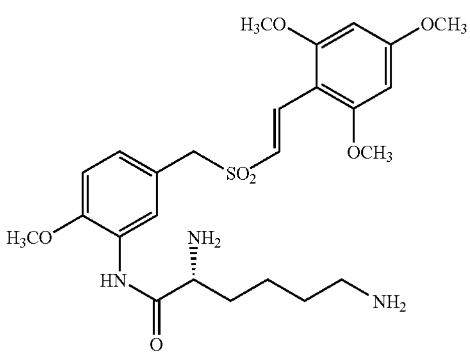 | (E)-2,4,6-Trimethoxystyryl-3-amino-4-methoxybenzyl-sulfone-L-lysineamide |
| 14 | 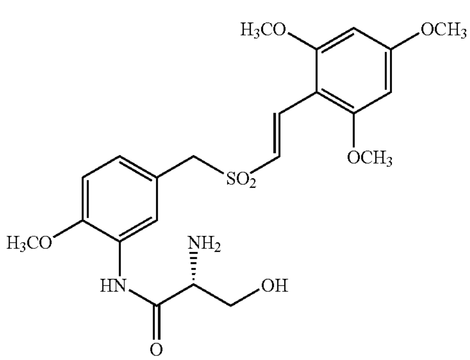 | (E)-2,4,6-Trimethoxystyryl-3-amino-4-methoxybenzyl-sulfone-L-serineamide |

TABLE 1-continued

| Compound | Structure | Name |
|---|---|---|
| 15 | 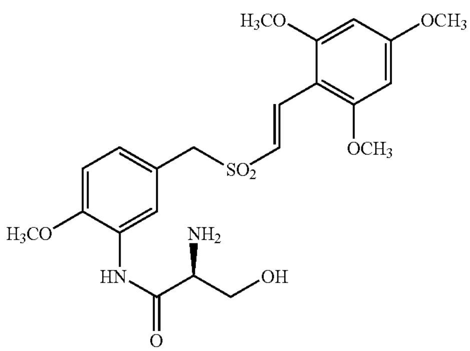 | (E)-2,4,6-Trimethoxystyryl-3-amino-4-methoxybenzyl-sulfone-D-serineamide |
| 16 | 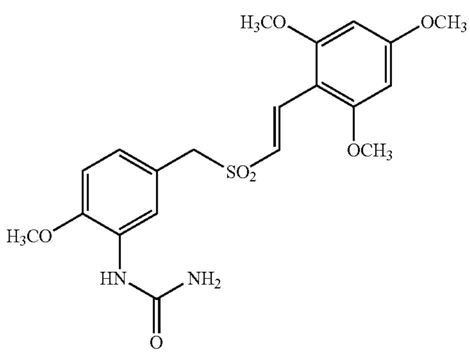 | (E)-2,4,6-Trimethoxystyryl-3-ureido-4-methoxybenzyl-sulfone |
| 17 | 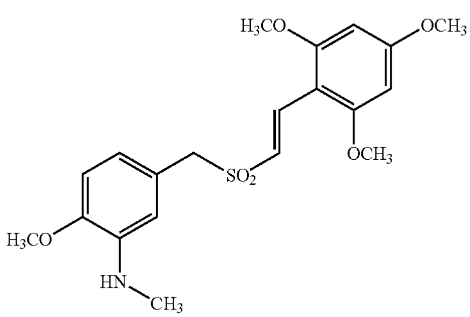 | (E)-2,4,6-Trimethoxystyryl-3-(N-methylamino)-4-methoxybenzylsulfone |
| 18 | 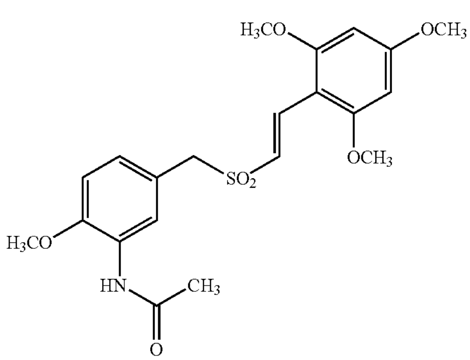 | (E)-2,4,6-Trimethoxystyryl-3-(acetamido)-4-methoxy-benzylsulfone |

TABLE 1-continued

| Compound | Structure | Name |
|---|---|---|
| 19 | 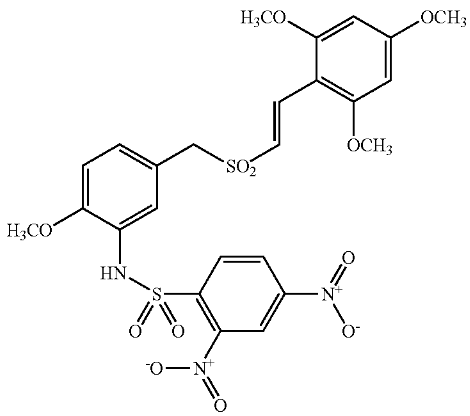 | (E)-2,4,6-Trimethoxystyryl-3-(2,4-dinitrobenzene-sulfamyl)-4-methoxybenzyl-sulfone |
| 20 | 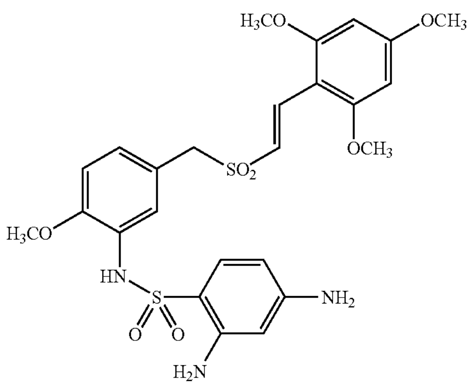 | (E)-2,4,6-Trimethoxystyryl-3-(2,4-diaminobenzene-sulfamyl)-4-methoxybenzyl-sulfone |
| 21 | 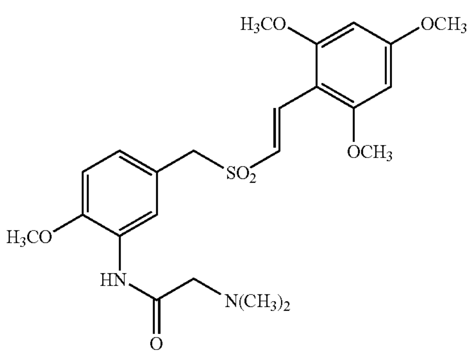 | (E)-2,4,6-trimethoxystyryl-3-(dimethylaminoacetamido)-4-methoxybenzylsulfone |
| 22 | 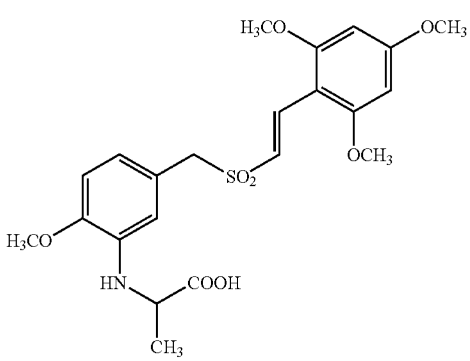 | (E)-2,4,6-trimethoxystyryl-3-(1-carboxyethyl)amino-4-methoxybenzylsulfone |

TABLE 1-continued

| Compound | Structure | Name |
|---|---|---|
| 23 | 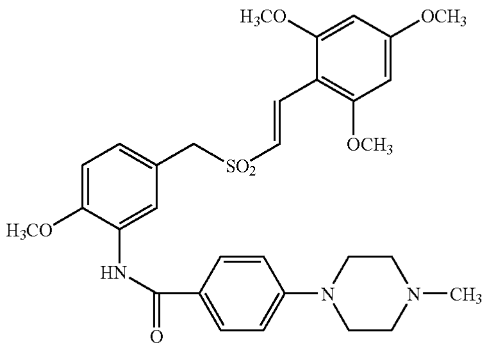 | (E)-2,4,6-trimethoxystyryl-3-[4-(4-methylpiperazin-1-yl)-benzamido]-4-methoxy-benzylsulfone |
| 24 | 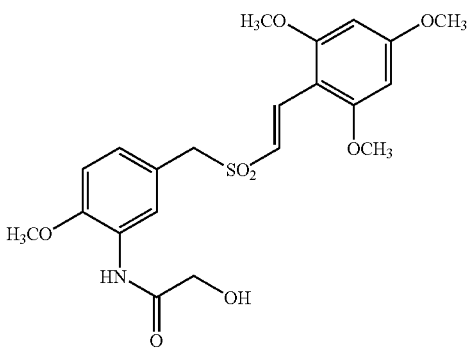 | (E)-2,4,6-trimethoxystyryl-3-(hydroxyacetamido)-4-methoxybenzylsulfone |
| 25 | 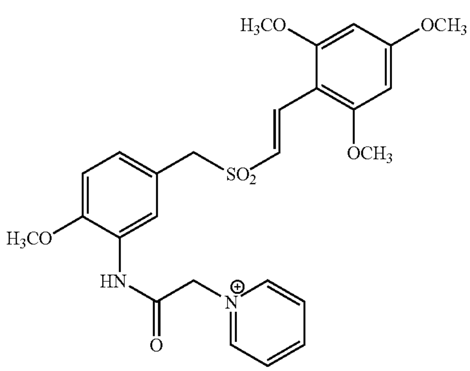 | (E)-2,4,6-trimethoxystyryl-3-[(pyridinium-1-yl)-acetamido]-4-methoxy-benzylsulfone |
| 26 | 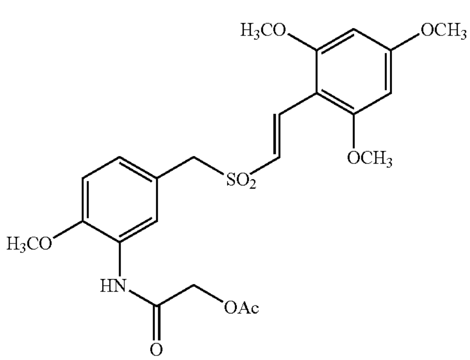 | (E)-2,4,6-trimethoxystyryl-3-(acetoxyacetamido)-4-methoxybenzylsulfone |

TABLE 1-continued

| Compound | Structure | Name |
|---|---|---|
| 27 | 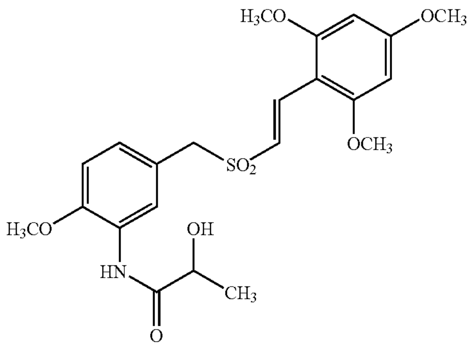 | (E)-2,4,6-Trimethoxystyryl-3-(2-hydroxypropionamido)-4-methoxybenzylsulfone |
| 28 | 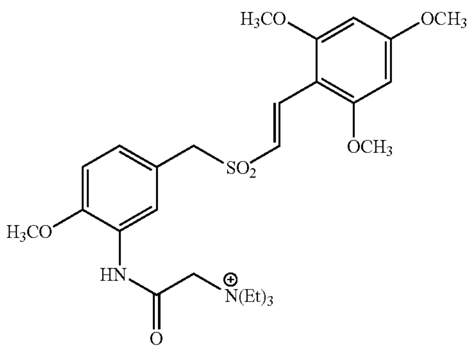 | (E)-2,4,6-trimethoxystyryl-3-(triethylammonium-acetamido)-4-methoxy-benzylsulfone |
| 29 | 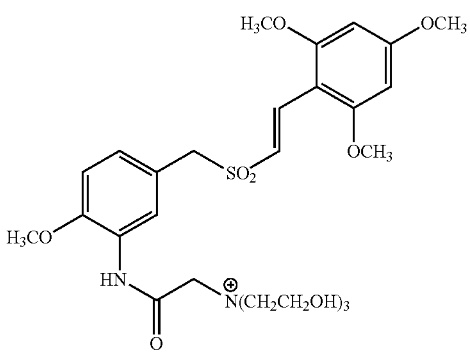 | (E)-2,4,6-trimethoxystyryl-3-[tri-(2-hydroxyethyl)-ammoniumacetamido]-4-methoxybenzylsulfone |
| 30 | 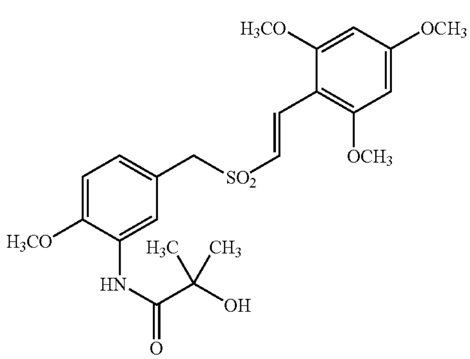 | (E)-2,4,6-trimethoxystyryl-3-(2-methyl-2-hydroxy-propionamido)-4-methoxy-benzylsulfone |

TABLE 1-continued

| Compound | Structure | Name |
|---|---|---|
| 31 | 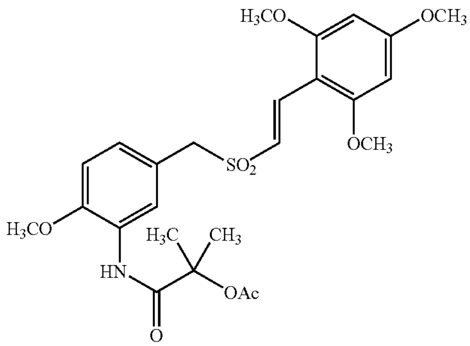 | (E)-2,4,6-trimethoxystyryl-3-(2-methyl-2-acetoxypropion-amido)-4-methoxybenzyl-sulfone |
| 32 | 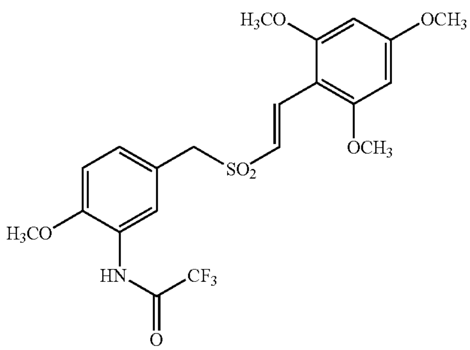 | (E)-2,4,6-trimethoxystyryl-3-(trifluoroacetamido)-4-methoxybenzylsulfone |
| 33 | 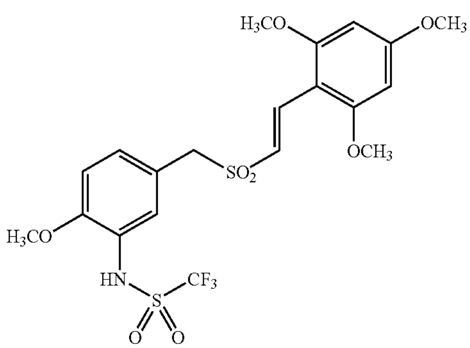 | (E)-2,4,6-trimethoxystyryl-3-(trifluoromethanesulfon-amido)-4-methoxybenzyl-sulfone |
| 34 | 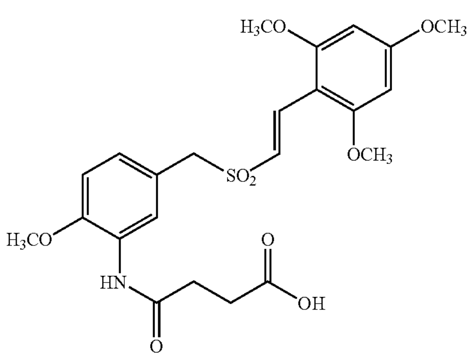 | (E)-2,4,6-trimethoxystyryl-3-(succinamido)-4-methoxy-benzylsulfone |

TABLE 1-continued

| Compound | Structure | Name |
|---|---|---|
| 35 | 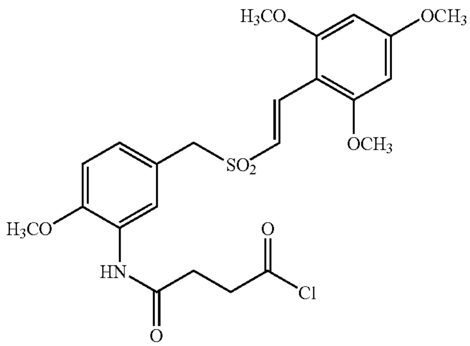 | (E)-2,4,6-trimethoxystyryl-3-(chlorosuccinamido)-4-methoxybenzylsulfone |
| 36 | 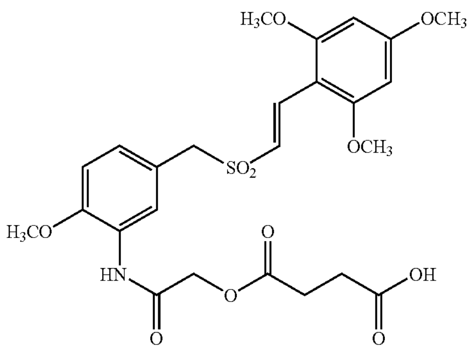 | (E)-2,4,6-trimethoxystyryl-3-(3-((3-carboxypropanoyl-oxy)acetamido)-4-methoxy-benzylsulfone |
| 37 | 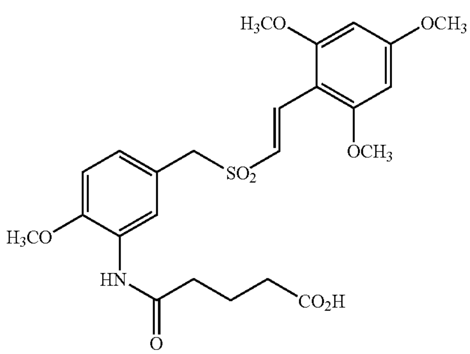 | (E)-2,4,6-trimethoxystyryl-3-(3-glutaramido)-4-methoxybenzylsulfone |
| 38 | 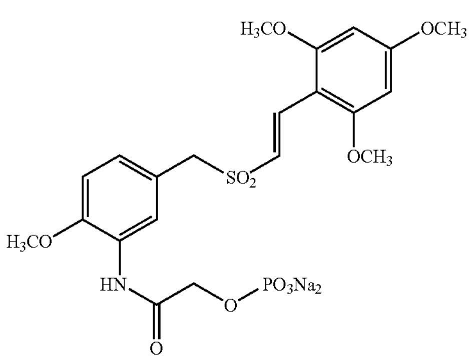 | (E)-2,4,6-trimethoxystyryl-3-(phosphonatoacetamido)-4-methoxybenzylsulfone, disodium salt |

TABLE 1-continued

| Compound | Structure | Name |
|---|---|---|
| 39 | 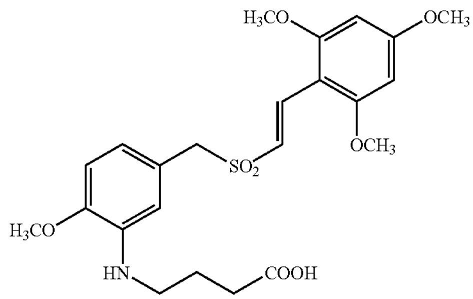 | (E)-2,4,6-trimethoxystyryl-3-(3-carboxypropylamino)-4-methoxybenzylsulfone: |
| 40 | 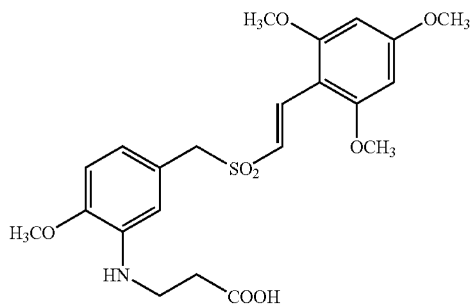 | (E)-2,4,6-trimethoxystyryl-3-(2-carboxyethylamino)-4-methoxybenzylsulfone |
| 41 | 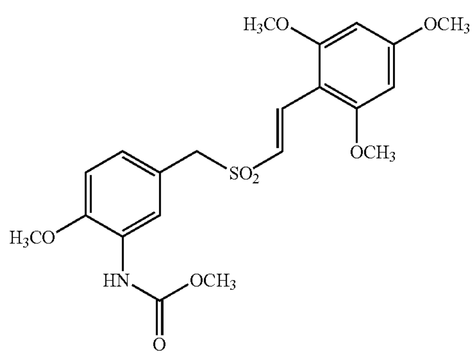 | (E)-2,4,6-trimethoxystyryl-3-(methylcarbamoyl)-4-methoxybenzylsulfone |
| 42 | 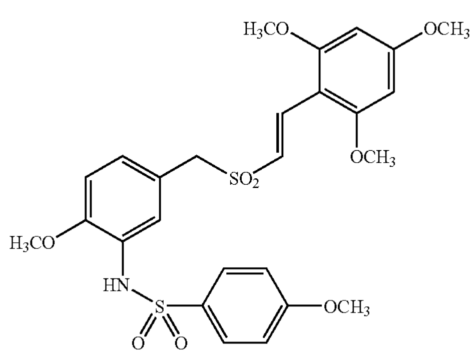 | (E)-2,4,6-Trimethoxystyryl-3-(4-methoxybenzene-sulfamyl)-4-methoxybenzyl-sulfone |

TABLE 1-continued

| Compound | Structure | Name |
|---|---|---|
| 43 | 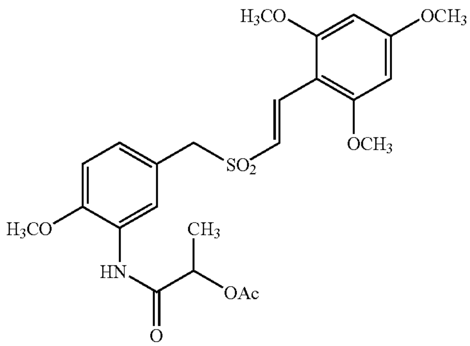 | (E)-2,4,6-trimethoxystyryl-3-(2-acetoxypropionamido)-4-methoxybenzylsulfone |
| 44 | 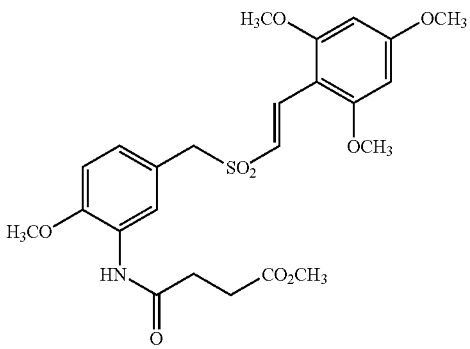 | (E)-2,4,6-trimethoxystyryl-3-(methylsuccinamido)-4-methoxybenzylsulfone |
| 45 | 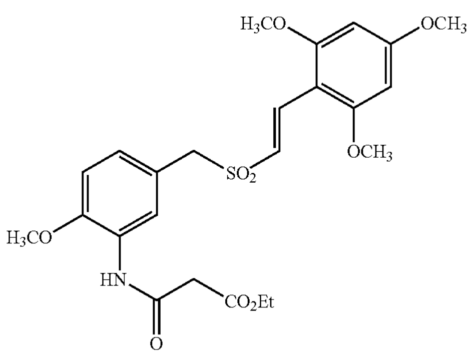 | (E)-2,4,6-trimethoxystyryl-3-(ethylmalonamido)-4-methoxybenzylsulfone |
| 46 | 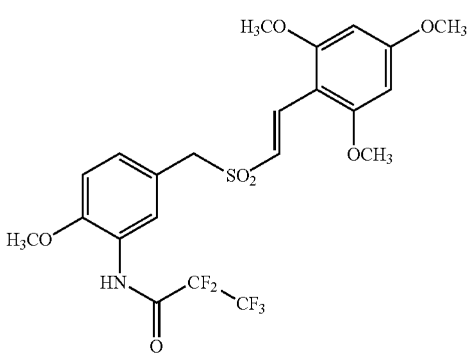 | (E)-2,4,6-Trimethoxystyryl-3-(pentafluoropropionamido)-4-methoxybenzylsulfone |

TABLE 1-continued
| Compound | Structure | Name |
|---|---|---|
| 47 | 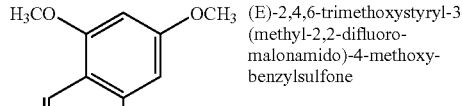 | (E)-2,4,6-trimethoxystyryl-3-(methyl-2,2-difluoro-malonamido)-4-methoxy-benzylsulfone |
| 48 | 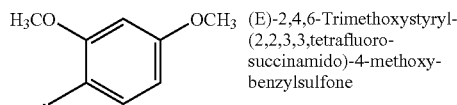 | (E)-2,4,6-Trimethoxystyryl-3-(2,2,3,3,tetrafluoro-succinamido)-4-methoxy-benzylsulfone |
| 49 | 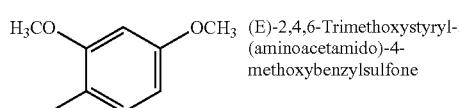 | (E)-2,4,6-Trimethoxystyryl-3-(aminoacetamido)-4-methoxybenzylsulfone |
| 50 | 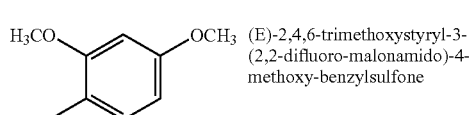 | (E)-2,4,6-trimethoxystyryl-3-(2,2-difluoro-malonamido)-4-methoxy-benzylsulfone |

TABLE 1-continued

| Compound | Structure | Name |
|---|---|---|
| 51 | 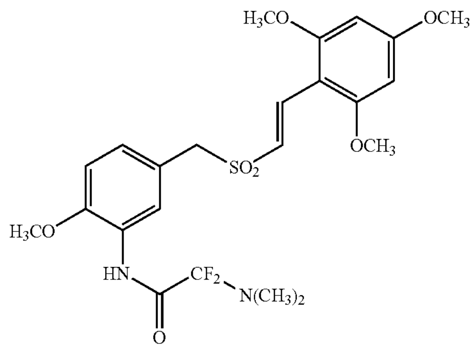 | (E)-2,4,6-trimethoxystyryl-3-(dimethylamino-α,α-difluoroacetamido)-4-methoxybenzylsulfone |

Pharmacologically active salts of these compounds are preferred, particularly sodium (Na) salts. Development compound ON 01910.Na (NOVONEX™), is a most preferred highly potent kinase inhibitor that has applications in cancer and other disease areas ((E)-2,4,6-trimethoxystyryl-3-carboxymethylamino-4-methoxybenzylsulfone). The sodium salt of the compound, as illustrated, also designated ON 01910.Na, is the most preferred salt for use in formulations of the present invention:

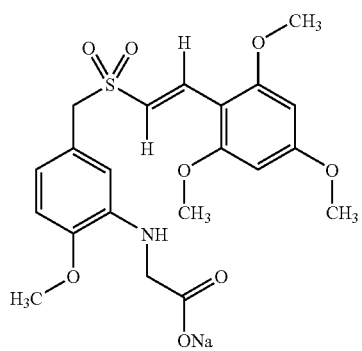

Empirical formula $=C_{21}H_{24}NO_8SNa$. Molecular weight=473.47. Although the compound is hydrophobic, the Na salt, as shown, is very soluble. The sodium salt is an off-white to yellow amorphous solid that readily absorbs water after complete drying. The drug substance may be hydrated with up to 3, for example, or up to 4 moles of water. The molecule also can form solvates with other solvents. See, FIG. 1, Example I. Example Reaction Scheme (ON 01910.Na Clinical Material method of synthesis). Synthesis is started with 2,4,6,-trimethoxy-benzaldehyde (Hunan Xinyu, Changsha, China) and 3-nitro-4-methoxybenzylsulfonylacetic acid (ChemPacific, Hangzhou, China).

II. Formulations

Compositions of the present invention improve the stability, solubility, and efficacy of amino-substituted (e)-2,6-dialkoxystyryl 4-substituted benzylsulfones substituted compounds. These compounds exhibit a broad range of activity in a wide array of cancer cells. Provided herein are compositions that provide for solubilization and stabilization of these compounds as well as for their efficacious delivery by means of parenteral administration for the prevention and/or treatment of cancer and related proliferative disorders.

The term "effective amount", as used herein refers to an amount of a compound within the description of the present disclosure which, upon parenteral administration to a mammal in a composition of the present invention, is capable of providing a therapeutic effect to a mammal in need thereof. "Therapeutic effect", as used herein, refers to the ability to prevent, control, or treat a pathophysiological or disease condition, for example, a disorder related to abnormal cell growth and/or proliferation.

Compositions described herein are generally formulated to comprise at least one of the compounds within a range of about 10 mg/ml to about 400 mg/ml. Preferred compositions of the present invention comprise at least one compound within the scope of the description at a concentration within the range of about 25 mg/ml to about 250 mg/ml. Compositions described herein are formulated to comprise at least one of the compounds within the scope of the description at a concentration within the range of about 40 mg/ml to about 200 mg/ml. Compositions described herein are also formulated to comprise at least one of the compounds within the scope of the description at a concentration within the range of about 50 mg/ml to about 150 mg/ml. Compositions described herein are particularly formulated to comprise at least one of the compounds within the scope of the description at a concentration within the range of about 60 mg/ml to about 100 mg/ml. Compositions described herein are formulated to comprise at least one of the compounds within the scope of the description at a concentration of about 75 mg/ml.

Compositions of the present invention are generally formulated with the active ingredients, i.e., the compounds, in a concentrated form for storage and handling prior to dilution with suitable parenteral diluent prior to infusion. A single dosage is generally within the range of about 1 ml to about 5 ml of any of the compositions described herein. 3 ml individual dosages of compositions described herein are preferred. The dosages may be packaged, for example, in 5 ml vials.

Compositions of the present invention may, for example, be diluted with about 7 parts diluent (7:1) prior to administration (e.g., the formulation which is 75/mg/ml in 50% PEG (Example II)). However, the dilution factor and the diluent employed depend on the concentration of drug in the formulation, and the composition of the vehicle, i.e., whether the formulation contains, for example, about 25%, more than 25% (other than 25%, e.g., about 28%), about 30%, about 35%, about 40%, about 42.5% about 45%, about 47.5%, about 50%, about 52.5%, about 55%, about 57.5%, about 60%, about 65%, about 70%, about 75%, about 80% or about 100% PEG (as well as values in between). Compositions of the present invention, however, may be diluted with anywhere within the range of about 2 volumes of suitable parenteral diluent prior to infusion to about 12 volumes of suitable parenteral diluent, prior to infusion. The final diluted product for parenteral administration of compositions of the present invention should have a pH within the range of about 5.0 to about 9.0. Preferably the final diluted product for parenteral administration should have a pH within the range of about 7.0 to about 7.5. A final diluted product pH of about 7.4 is preferred. The osmolarity of the diluted formulation for administration should be approximately within the range of about 200 to about 400 mOsm/kg. Preferred osmolarity of the diluted formulation for administration should be approximately within the range of about 270 to about 330 mOsm/kg. A preferred osmolarity of the diluted formulation for administration should be approximately 300 mOsm/kg.

Dielectric Constant

Compositions of the present invention, compared to conventional formulations, are demonstrated herein to unexpectedly greatly increase the solubility and stability of the specifically described compounds and hence significantly increase the efficacy and therapeutic value upon parenteral administration. A dramatic stabilization effect, however, is observed by lowering the dielectric constant of the formulation vehicle. The effect of the dipole moment of solvent on the compounds described herein is found to be an extraordinary factor in the formulation of compositions for efficacious parenteral delivery of the compounds, particularly for efficacy. The influence of ionic strength and dielectric constant on the stabilization of the activated complex in the transition state of these compounds is paramount in formulating efficacious compositions for parenteral administration.

Compositions for parenteral administration are particularly provided which comprise an effective amount of a compound of formula I or a compound of formula IL and at least about 25% (certain exemplary embodiments comprise about 50%, e.g., between about 40% and about 60%) by weight of at least one water soluble polymer, wherein formula I:

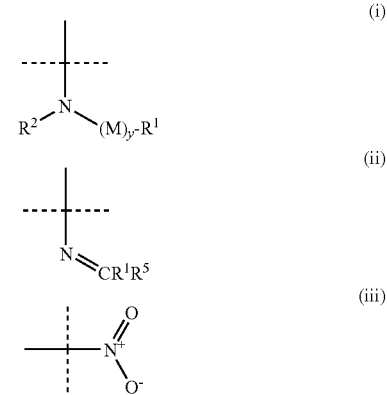

I

X is selected from the group consisting of (i) and (ii) below:

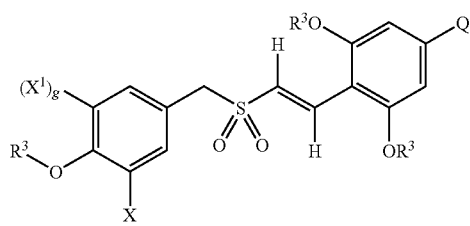

(i)

(ii)

$X^1$ is selected from the group consisting of (i), (ii) and (iii) below:

(i)

(ii)

(iii)

wherein $X^1$ is optionally protected with one or more chemical protecting groups;

g is 0 or 1;

each M is a bivalent connecting group independently selected from the group consisting of —($C_1$-$C_6$)alkylene-, —$(CH_2)_a$—V—$(CH_2)_b$, —$(CH_2)_d$—W—$(CH_2)_e$— and —Z—;

each y is independently selected from the group consisting of 0 and 1;

each V is independently selected from the group consisting of arylene, heteroarylene, —C(=O)—, —C(=S)—, —S(=O)—, —$SO_2$, —C(=O)O—; —C(=O)($C_1$-$C_6$)perfluoroalkylene-, —C(=O)$NR^4$—, —C(=S)$NR^4$— and —$SO_2NR^4$—;

each W is independently selected from the group consisting of —$NR^4$—, —O— and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

—Z— is

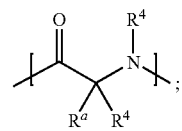

wherein the absolute stereochemistry of —Z— is D or L or a mixture of D and L;

each $R^a$ is independently selected from the group consisting of —H, —($C_1$-$C_6$)alkyl, —$(CH_2)_3$—NH—C($NH_2$)(=NH), —$CH_2$C(=O)$NH_2$, —$CH_2$COOH, —$CH_2$SH, —$(CH_2)_2$C(=O)—$NH_2$, —$(CH_2)_2$COOH, —$CH_2$-(2-imidazolyl), —CH($CH_3$)—$CH_2$—$CH_3$, —$CH_2$CH($CH_3$)$_2$, —$(CH_2)_4$—$NH_2$, —$(CH_2)_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring;

each $R^1$ is independently selected from the group consisting of —H, unsubstituted aryl, substituted aryl, substituted heterocyclic, unsubstituted heterocyclic, —$CO_2R^5$, —$C(=O)NR^4{}_2$, —$CR^4R^6R^7$, —$C(=NH)$—$NR^4{}_2$, —($C_1$-$C_6$)perfluoroalkyl, —$CF_2Cl$, —$P(=O)(OR^4)_2$, —$OP(=O)(OR^4)_2$ and a monovalent peptidyl moiety with a molecular weight of less than 1000; provided that when y is 0 and $R^1$ is —$CO_2R^5$, $R^5$ is not —H;

each $R^2$ is independently selected from the group consisting of —H, —($C_1$-$C_6$)alkyl, and aryl($C_1$-$C_3$)alkyl, wherein —$R^2$ and -$(M)_y$-$R^1$ may optionally be linked covalently to form a 5-, 6- or 7-membered substituted or unsubstituted heterocycle;

each $R^3$ is independently selected from —($C_1$-$C_6$)alkyl;

each $R^4$ is independently selected from the group consisting of —H, and —($C_1$-$C_6$)alkyl;

each $R^5$ is independently selected from the group consisting of —H, —($C_1$-$C_6$)alkyl and —($C_1$-$C_6$)acyl;

each $R^6$ is independently selected from the group consisting of —H, —($C_1$-$C_6$)alkyl, —$CO_2R^5$, —$C(=O)R^7$, —$OR^5$, —$OC(=O)(CH_2)_2CO_2R^5$, —$SR^4$, guanidino, —$NR^4{}_2$, —$NR^4{}_3{}^+$, —$N^+(CH_2CH_2OR^5)_3$, phenyl, substituted phenyl, heterocyclic, substituted heterocyclic and halogen;

each $R^7$ is independently selected from the group consisting of —$R^a$, halogen, —$NR^4{}_2$, and heterocycles containing two nitrogen atoms; and Q is selected from the group consisting of —H, —($C_1$-$C_6$) alkoxy, halogen, —($C_1$-$C_6$)alkyl and —$NR^4{}_2$;

wherein the substituents for the substituted aryl and substituted heterocyclic groups comprising or included within R', $R^2$, $R^a$, $R^6$ and $R^7$, are independently selected from the group consisting of halogen, ($C_1$-$C_6$)alkyl, —$NO_2$, —CN, —$CO_2R^5$, —$C(=O)O(C_1$-$C_3$)alkyl, —$OR^5$, —($C_2$-$C_6$)—OH, phosphonato, —$NR^4{}_2$, —$NHC(=O)(C_1$-$C_6$)alkyl, sulfamyl, —$OC(=O)(C_1$-$C_3$)alkyl, —$O(C_2$-$C_6$)—$N((C_1$-$C_6$)alkyl)_2$ and —$CF_3$;

provided (1) when $R^1$ is a monovalent peptidyl moiety of molecular weight less than 1000 and V is —$C(=O)$—, —$C(=S)$—, —$S(=O)$— or —$SO_2$—, and b is 0;

then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —$C(=O)NR^3$—, —$SO_2NR^3$—, or —$NR^4$—, and b is 0, then said peptidyl moiety is coupled to M through the carboxy terminus of the peptidyl moiety or through a sidechain carboxyl group to form an imide, sulfonimide, or carboxamide respectively; and (3) when $R^1$ is a monovalent peptidyl moiety of molecular weight less than 1000 and W is —S— or —O—, and d is 0, then said peptidyl moiety is coupled to M through the carboxy terminus of the peptidyl moiety or through a sidechain carboxyl group to form a carbothioic acid ester or the carboxylic ester respectively; and, wherein formula IIa:

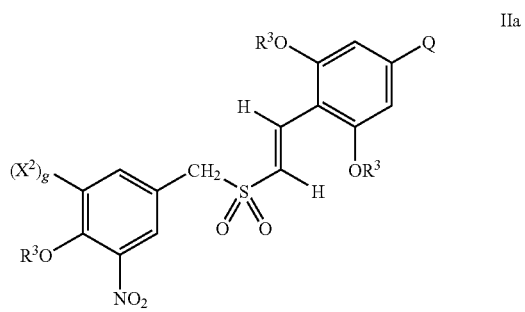

g is 0 or 1;

each $R^3$ is independently selected from —($C_1$-$C_6$)alkyl;

each $R^4$ is independently selected from the group consisting of —H and —($C_1$-$C_6$)alkyl;

Q is selected from the group consisting of —H, —($C_1$-$C_6$) alkoxy, halogen, —($C_1$-$C_6$)alkyl and —$NR^4{}_2$; and $X^2$ is selected from the group consisting of $NO_2$ and —$NH_2$, optionally protected with a chemical protecting group, or a pharmaceutically effective salt, prodrug, or metabolite thereof.

Preferred compounds for formulation in compositions of the present invention include but are not limited to (E)-2,4,6-trimethoxystyryl-3-[4-(4-methylpiperazin-1-yl) benzamido]-4-methoxy-benzylsulfone;

(E)-2,4,6-trimethoxystyryl-3-(acetoxyacetamido)-4-methoxybenzylsulfone;

(E)-2,4,6-trimethoxystyryl-3-(triethylammoniumacetamido)-4-methoxybenzyl-sulfone;

(E)-2,4,6-trimethoxystyryl-3-[tri-(2-hydroxyethylammonium)acetamido]-4-methoxy-benzylsulfone;

(E)-2,4,6-trimethoxystyryl-3-(2-methyl-2-hydroxypropionamido)-4-methoxybenzyl-sulfone;

(E)-2,4,6-trimethoxystyryl-3-(2-methyl-2-acetoxypropionamido)-4-methoxybenzyl-sulfone;

(E)-2,4,6-trimethoxystyryl-3-(2-acetoxypropionamido)-4-methoxybenzylsulfone;

(E)-2,4,6-trimethoxystyryl-3-(trifluoroacetamido)-4-methoxybenzylsulfone;

(E)-2,4,6-trimethoxystyryl-3-(trifluoromethanesulfonamido)-4-methoxybenzyl-sulfone;

(E)-2,4,6-trimethoxystyryl-3-[3-(3-carboxypropanoyloxy) acetamido]-4-methoxy-benzylsulfone;

(E)-2,4,6-trimethoxystyryl-3-(diethylphosphonatoacetamido)-4-methoxybenzyl-sulfone;

(E)-2,4,6-trimethoxystyryl-3-(phosphonatoacetamido)-4-methoxybenzylsulfone, disodium salt;

(E)-2,4,6-trimethoxystyryl-3-(methylcarbamoyl)-4-methoxybenzylsulfone;

(E)-2,4,6-trimethoxystyryl-3-(pentafluoropropionamido)-4-methoxybenzylsulfone;

(E)-2,4,6-trimethoxystyryl-3-[(methyl-(2,2-difluoro)malonamido)-4-methoxybenzyl-sulfone;

(E)-2,4,6-trimethoxystyryl-3-(2,2-difluoro-malonamido)-4-methoxybenzylsulfone;

(E)-2,4,6-trimethoxystyryl-3-(dimethylamino-α,α-difluoroacetamido)-4-methoxy-benzylsulfone;

(E)-2,4,6-trimethoxystyryl-3-(2,2,3,3-tetrafluoroethylsuccinamido)-4-methoxy-benzylsulfone;

(E)-2,4,6-trimethoxystyryl-4-methoxy-3-aminobenzylsulfone;

(E)-2,4,6-trimethoxy-styryl-4-methoxy-3-nitrobenzylsulfone;

(E)-2,4,6-trimethoxystyryl-3-(carboxyacetamido)-4-methoxybenzylsulfone;
(E)-2,4,6-trimethoxystyryl-3-(3,5-dinitrobenzamido)-4-methoxybenzyl-sulfone;
(E)-2,4,6-trimethoxystyryl-3-(3,5-diaminobenzamido)-4-methoxybenzyl-sulfone;
(E)-2,4,6-trimethoxystyryl-3-(chloroacetamido)-4-methoxybenzylsulfone;
(E)-2,4,6-trimethoxystyryl-3-[(4-methylpiperazinyl)acetamido]-4-methoxy-benzylsulfone;
(E)-2,4,6-trimethoxystyryl-3-(benzamido)-4-methoxybenzylsulfone;
(E)-2,4,6-trimethoxystyryl-3-(4-nitrobenzamido)-4-methoxybenzylsulfone;
(E)-2,4,6-trimethoxystyryl-3-(4-aminobenzamido)-4-methoxybenzylsulfone;
(E)-2,4,6-trimethoxystyryl-3-(acetamido)-4-methoxybenzylsulfone;
(E)-2,4,6-trimethoxystyryl-3-(dimethylaminoacetamido)-4-methoxybenzyl-sulfone;
(E)-2,4,6-trimethoxystyryl-3-(hydroxyacetamido)-4-methoxy-benzylsulfone;
(E)-2,4,6-trimethoxystyryl-3-(2-hydroxypropionamido)-4-methoxy-benzylsulfone;
(E)-2,4,6-trimethoxystyryl-3-(pyridinium-1-yl)acetamido-4-methoxybenzyl-sulfone;
(E)-2,4,6-trimethoxystyryl-3-(ethylmalonamido)-4-methoxy-benzylsulfone;
(E)-2,4,6-trimethoxystyryl-3-(glutaramido)-4-methoxybenzylsulfone;
(E)-2,4,6-trimethoxystyryl-3-(methylsuccinamido)-4-methoxybenzylsulfone;
(E)-2,4,6-trimethoxystyryl-3-(succinamido)-4-methoxybenzylsulfone;
(E)-2,4,6-trimethoxystyryl-3-(3-chlorosuccinamido)-4-methoxybenzyl-sulfone;
(E)-2,4,6-trimethoxystyryl-3-(aminoacetamido)-4-methoxybenzylsulfone;
(E)-2,4,6-trimethoxystyryl-3-amino-4-methoxybenzylsulfone-L-lysineamide;
(E)-2,4,6-trimethoxystyryl-3-amino-4-methoxybenzylsulfone-L-serineamide;
(E)-2,4,6-trimethoxystyryl-3-amino-4-methoxybenzylsulfone-D-serineamide;
(E)-2,4,6-trimethoxystyryl-3-(carboxymethylsulfamyl)-4-methoxybenzyl-sulfone;
(E)-2,4,6-trimethoxystyryl-3-(4-methoxybenzenesulfamyl)-4-methoxy-benzylsulfone;
(E)-2,4,6-trimethoxystyryl-3-(2,4-dinitrobenzenesulfamyl)-4-methoxybenzyl-sulfone;
(E)-2,4,6-trimethoxystyryl-3-(2,4-diaminobenzenesulfamyl)-4-methoxy-benzylsulfone;
(E)-2,4,6-trimethoxystyryl-3-guanidino-4-methoxybenzylsulfone;
racemic-(E)-2,4,6-trimethoxystyryl-3-(1-carboxyethyl)amino-4-methoxy-benzylsulfone;
D-(E)-2,4,6-trimethoxystyryl-3-(1-carboxyethyl)amino-4-methoxybenzyl-sulfone;
L-(E)-2,4,6-trimethoxystyryl-3-(1-carboxyethyl)amino-4-methoxybenzyl-sulfone;
(E)-2,4,6-trimethoxy-styryl-3-(carboxymethylamino)-4-methoxybenzyl-sulfone;
(E)-2,4,6-trimethoxy-styryl-3-(N-methylamino)-4-methoxybenzylsulfone;
(E)-2,4,6-trimethoxystyryl-3-(4-nitrophenylimino)-4-methoxybenzylsulfone;
(E)-2,4,6-trimethoxy-styryl-3-(ureido)-4-methoxybenzylsulfone;
racemic-(E)-2,4,6-trimethoxystyryl-3-(1-carboxyethyl)amino-4-methoxy-benzylsulfone;
D-(E)-2,4,6-trimethoxystyryl-3-(1-carboxyethyl)amino-4-methoxy-benzylsulfone;
L-(E)-2,4,6-trimethoxystyryl-3-(1-carboxyethyl)amino-4-methoxy-benzylsulfone;
(E)-2,4,6-trimethoxystyryl-3-carboxymethylamino-4-methoxybenzylsulfone;
(E)-2,4,6-trimethoxystyryl-3-(3-carboxypropylamino)-4-methoxybenzyl-sulfone; and
(E)-2,4,6-trimethoxystyryl-3-(2-carboxyethylamino)-4-methoxybenzyl-sulfone;
and pharmaceutically acceptable salts thereof.

The term "water soluble polymer", as used herein, includes but is not limited to polyethylene glycol (PEG), poly-oxyethylene, poly-oxyethylene-poly-oxypropylene copolymer, polyglycerol, polyvinylalcohol, polyvinylpyrrolidone (PVP), polyvinylpyridine N-oxide, copolymer of vinylpyridine N-oxide and vinyl-pyridine, and the like, as well as derivatives thereof, and combinations thereof.

Poly-oxyethylene and/or poly-oxyethylene-poly-oxypropylene copolymers are example water-soluble polymers for use in formulations of the present invention. Poloxamer 407 (e.g., Pluronic F 127, Lµtrol® micro 127), for example, and/or Poloxamer 188 (e.g., Pluronic F 68, Lµtrol® micro 68) are poly-oxyethylene-poly-oxypropylene copolymers that can be used independently or in combination in formulations of the present invention. BASF Corporation, Mount Olive, N.J.

Lower dielectric constant moreover unexpectedly increases stability of ON 1910.Na, for example.

Polyethylene glycols (PEGs) are preferred water soluble polymers. Low molecular weight liquid polyethylene glycols, for example, PEG 300, PEG 400, PEG 600, and PEG 800, are preferred water soluble polymers that can be used independently or in combination with each other, for example, in formulations of the present invention. Particularly preferred are PEG 300, PEG 400, and PEG 600. Lutrol® E 300, Lutrol® E 400 and Lutrol® E 600, for example, are commercially available from BASF Corporation, Mount Olive, N.J. PEG 400 (Polyethylene glycol 400, Macrogol 400, PEG 400, Poly(oxy-1,2-ethanediyl),alpha-hydro-omega-hydroxy-(CAS No: 25322-68-3)), e.g., Lutrol® E 400, is most preferred.

Compositions of the present invention are preferred wherein the water soluble polymer is selected from the group consisting essentially of PEG 300, PEG 400, PEG 600, and PEG 800. Although not specifically listed here PEG products substantially the same, otherwise within this characteristic range of PEG entities, may be employed in compositions of the present invention.

Aqueous compositions for parenteral administration of a compound described herein, or a pharmaceutically effective salt, prodrug, or metabolite thereof, are provided which comprise (prior to dilution for parenteral administration) at least about 25% by weight of at least one water soluble polymer. Aqueous compositions of the present invention comprise at least about 25% by weight of at least one water soluble polymer. Embodiment compositions of the present invention described herein, for example, comprise about 25%, about 30%, about 35%, about 40%, about 42.5% about 45%, about 47.5%, about 50%, about 52.5%, about 55%, about 57.5%, about 60%, about 65%, about 70%, about 75%, about 80% or about 100% (as well as values in between) by weight of at least one water soluble polymer. Aqueous compositions of the present invention prior to dilution for parenteral administration preferably have a pH within the range of about pH 8 to about pH 14. Formulation composition embodiments described herein particularly exhibit pH values, for example, of about 8, about 8.5, about 9, about 9.25, about 9.5, about 9.75, about 10, about 10.25, about 10.5, about 10.75, about 11, about 11.25, about 11.5, about 11.75, about 12, about 12.25, about 12.5, about 12.75, about 13, about 13.25, about 13.5, about 13.75 and about 14 (as well as values in between). As a general statement, the higher the pH the more stable will be the formulation. Aqueous compositions of the present invention generally comprise an effective amount of at least one compound described herein, at least one water soluble polymer, water, and a buffer. The strength of the buffer is important. Higher buffer strengths resist the change in pH. Hence, higher the buffer strength the more stable will be the formulation. Means to increase buffer strength, e.g., incremental increase in buffer molarity, are well-known in the art of formulations. Preferred buffers are generally selected from the group consisting of biologically acceptable buffers, including but not limited to pyridine (pKa −5.23), piperazine (5.55), MES (6.21), BIS-TRIS (6.46), ADA (6.62), ACES (6.91), PIPES (7.1), Phosphate (7.2), BES (7.26), MOPS (7.31), TES (7.61), TRIS (8.06), Ethanolamine (9.5), and buffers otherwise known and used in the art of parenteral formulations. A preferred buffer for use in compositions of the present invention is phosphate. Buffers, however, may contain an additional tonicity agent to make the formulation isoosmotic. Examples of tonicity agents include sodium chloride, mannitol, glucose, dextrose, and similar agents known in the art. Aqueous compositions of the present invention that have a higher pH, e.g., about 11, for example, generally provide for higher stability of the compounds described herein. Certain embodiments of these formulations described herein exhibit a pH between about 11 and about 14. Certain formulations described herein, for example, exhibit pH values between about 10.6 and about 13.6. Aqueous compositions of the invention are preferred which comprise an effective amount of at least one compound described herein and at least about 25% by weight of at least one water soluble polymer. Aqueous compositions of the invention are also preferred which comprise an effective amount of at least one compound described herein and at least about 40% by weight of at least one water soluble polymer, e.g., about 42.5% about 45%, about 47.5%, about 50%, about 52.5%, about 55%, about 57.5%, about 60%, about 65%, about 70%, about 75%. Aqueous compositions of the invention are preferred which comprise an effective amount of at least one compound described herein and at least about 32.5% by weight of at least one water soluble polymer. Aqueous compositions of the invention are further preferred which comprise an effective amount of at least one compound described herein and at least about 55% by weight of at least one water soluble polymer. Aqueous compositions of the invention can comprise an effective amount of at least one compound described herein and at least about 93% by weight of at least one water soluble polymer. Aqueous compositions of the present invention that comprise PEG 400 are preferred. Aqueous compositions of the present invention are particularly preferred that have a high pH (between about 8 and about 14) and that comprise an effective amount of at least one compound described herein and/or a pharmaceutically effective salt, prodrug, or metabolite thereof and at least about 40% by weight of PEG 400.

The results of formulation studies demonstrate that the stability of (E)-2,4,6-trimethoxystyryl-3-carboxymethylamino-4-methoxybenzylsulfone (ON 01910.Na), for example, is improved in the presence of PEG 400. The stability is further increased by increasing the pH of the aqueous phase to a range between about 10 and about 13, and furthermore if the aqueous phase is buffered. Based on the results from formulation development efforts, a 50% PEG-400 formulation in a pH 10 was determined to provide suitable stability under refrigeration. Higher pH is preferred for long-term storage. Formulations were prepared with about 75 mg/ml of drug substance in the final formulation. An example substantially stable formulation of (E)-2,4,6-trimethoxystyryl-3-carboxymethylamino-4-methoxybenzylsulfone (ON 01910.Na) containing 50% PEG-400 in 0.016M phosphate buffer (Sodium Phosphate Dibasic), pH 10.0 is provided in Example II. The example formulation comprises 75 mg/ml (E)-2,4,6-trimethoxystyryl-3-carboxymethylamino-4-methoxybenzylsulfone (ON 01910.Na), 50% PEG-400 in 0.016 M phosphate buffer, pH 10. Dilution of this product 1:7 with 0.00025 M phosphoric acid, for example, yields a product that has a pH of 7.4 and osmolarity of approximately 300 mOsm/kg.

Water, however, is not a necessary element to formulate compositions of the present invention. A dramatic stabilization effect is unexpectedly observed by lowering the dielectric constant of the formulation vehicle. See, Example III. A shelf stable formulation was developed, for example, based on 100% PEG-400 and is demonstrated herein to have significantly greater stability than conventional formulations. See, Example IV. Accordingly, preferred compositions of the present invention consist essentially of an effective amount of at least one compound described herein, and/or a pharmaceutically effective salt, prodrug, or metabolite thereof, and at least one water soluble polymer. Compositions of the present invention consist essentially of, for example, an effective amount of at least one compound described herein, and/or a pharmaceutically effective salt, prodrug, or metabolite thereof, and at least one water soluble polymer selected from the group consisting essentially of polyethylene glycol (PEG), poly-oxyethylene, poly-oxyethylene-poly-oxypropylene copolymers, polyglycerol, polyvinylalcohol, polyvinylpyrrolidone (PVP), polyvinylpyridine N-oxide, copolymer of vinylpyridine N-oxide and vinylpyridine. Polyethylene glycols (PEGs), as discussed supra, are preferred water soluble polymers; particularly PEG 400. Accordingly, a preferred composition of the present invention consists essentially of an effective amount of at least one compound described herein, and/or a pharmaceutically effective amount of a salt, prodrug, or metabolite thereof, and PEG 400. Compounds described herein, e.g., ON 01910.Na, may be formulated, for example, within a range of about 25% to 100% PEG 400. Preferred compositions of the present invention comprise at least one amino-substituted (e)-2,6-dialkoxystyryl 4-substituted benzylsulfone, e.g., ON 01910.Na, and between about 35% and about 65% PEG 400.

An example composition of the present invention is 75 mg of the sodium salt of (E)-2,4,6-trimethoxystyryl-3-carboxymethylamino-4-methoxybenzylsulfone (ON 01910.Na) per ml in 100% PEG-400 (NF Grade). A single dose of the composition is generally within the range of about 1 ml to about 3 ml of the formulation. 1.5 ml of the sterile formulation, for example, is packaged in a sterile 5 ml vial. This formulation comprises about 6.5% wt. of the sodium salt of (E)-2,4,6-trimethoxystyryl-3-carboxymethylamino-4-methoxybenzylsulfone (ON 01910.Na)/wt. in 100% PEG 400. (E)-2,4,6-trimethoxystyryl-3-carboxymethylamino-4-methoxybenzylsulfone (ON 01910.Na) injection composition, for example, is a clear yellow viscous solution. It is supplied as a non-aqueous solution intended for dilution with suitable parenteral diluent prior to infusion. Each ml of sterile non-pyrogenic solution contains 75 mg (E)-2,4,6-trimethoxystyryl-3-carboxymethylamino-4-methoxybenzylsulfone (ON 01910.Na) in Polyethylene Glycol, 400, NF and is stable at 40° C. and below for at least 4 weeks.

This formulation, however, is recently demonstrated to be shelf-stable for over one year.

Safety and Efficacy of a Preferred Formulation of ON 01910.Na (Phase I Clinical Study)

Safety and efficacy of this formulation, for example, is tested in a Phase I clinical study, at The Johns Hopkins Sidney Kimmel Cancer Center, Baltimore, Md., i.e., "Phase I Dose Escalation Study Of ON 01910.Na By 2-Hour Intravenous Infusion In Patients With Advanced Solid Tumors". U.S. FDA IND #66,780. The objectives of this study include an identification of a maximum tolerated dose (MTD) and a recommended dose for further clinical studies. A further object of the study is to establish a safety profile, i.e., to observe any toxicities. The patients in this study have advanced solid tumors that have failed conventional treatments, or for which no approved therapy exists. An object of the study is particularly to observe efficacy (anti-cancer effects).

The patients are administered the preferred formulation described herein of the ON 01910.Na drug (properly diluted in intravenous solution) over a two hour period, twice per week, for three weeks. The patients are subsequently observed for ten days, to constitute a four week treatment cycle. If the patients have no drug related toxicity and their disease does not progress, they can continue with additional cycles of therapy.

This study started with a single patient at the first starting dose level of 80 mg per patient. If there is no grade 2 or worse drug-related toxicity (side effects) observed in the first four week cycle, then another patient may be dosed at the next higher dose level. The first patient was dosed at 80 mg per patient on Aug. 3, 2004. Since then, seven patients have been enrolled and treated at escalating dose levels, that is, at 160, 320, 480, 800, 1280, and most recently 2080 mg per patient. In each case, there were no grade 2 or worse toxicities, recently, an eighth patient will soon be enrolled and will be treated at 3120 mg, for example.

Current studies demonstrate that ON 01910.Na, for example, can be safely administered in this formulation, at least at doses up to 2080 mg given iv in a 2 hour infusion, twice per week, for 3 weeks, with subsequent ten days off, to constitute a four week cycle of treatment. Efficacy of this formulation, for example, has been observed in many mouse xenograft preclinical laboratory experiments.

Accordingly, an example composition of the present invention comprises about 6% to about 7% wt. (E)-2,4,6-trimethoxystyryl-3-carboxymethylamino-4-methoxybenzylsulfone (ON 01910.Na) and between about 35% and about 65% PEG-400 (NF Grade). Preferred compositions of the present invention comprise about 4% to about 10% wt. of at least one compound described herein, and/or a pharmaceutically effective amount of a salt, prodrug, or metabolite thereof, and between about 35% and about 65% PEG-400 (NF Grade). Particularly preferred compositions of the present invention comprise about 5% to about 8% wt. of at least one compound described herein, and/or a pharmaceutically effective amount of a salt, prodrug, or metabolite thereof, and between about 40% and about 60% PEG-400 (NF Grade). Preferred compositions of the present invention comprise about 6% to about 7% wt. of at least one compound described herein, and/or a pharmaceutically effective amount of a salt, prodrug, or metabolite thereof, and between about 45% and about 55% PEG-400 (NF Grade).

III. Methods of Use

A method for the prevention and/or treatment of a pathophysiological condition is provided which comprises parenterally administering an effective amount of a composition of the present invention to a mammal. A method for the prevention and/or treatment of a pathophysiological condition mediated by abnormal cell growth is provided which comprises parenterally administering an effective amount of a composition of the present invention to a mammal. A method for the prevention and/or treatment of a pathophysiological condition mediated by abnormal cell growth is provided which comprises parenterally administering an effective amount of a composition of the present invention to a mammal in need of therapeutic intervention to control the pathophysiological condition and wherein abnormal cell growth is controlled.

ON 1910 and other compounds described herein exhibit strong synergy, for example, with chemotherapeutic agents, often inducing complete regression of tumors.

A method of inhibiting growth of tumor cells in an individual afflicted with cancer is provided comprising administering to said individual an effective amount of a composition of the present invention. Compositions of the present invention inhibit the proliferation of tumor cells by inducing cell death. Compositions described herein are particularly useful to kill primary or metastatic tumor or neoplastic cells in cancers of at least the following histologic subtypes: sarcoma (cancers of the connective and other tissue of mesodermal origin); melanoma (cancers deriving from pigmented melanocytes); carcinoma (cancers of epithelial origin); adenocarcinoma (cancers of glandular epithelial origin); cancers of neural origin (glioma/glioblastoma and astrocytoma); and hematological neoplasias, such as leukemias and lymphomas (e.g., acute lymphoblastic leukemia, chronic lymphocytic leukemia, and chronic myelocytic leukemia). Compositions of the present invention eliminate primary or metastatic tumor or neoplastic cells in cancers having their origin in at least the following organs or tissues, regardless of histologic subtype: breast; tissues of the male and female urogenital system (e.g. ureter, bladder, prostate, testis, ovary, cervix, uterus, vagina); lung; tissues of the gastrointestinal system (e.g., stomach, large and small intestine, colon, rectum); exocrine glands such as the pancreas and adrenals; tissues of the mouth and esophagus; brain and spinal cord; kidney (renal); pancreas; hepatobiliary system (e.g., liver, gall bladder); lymphatic system; smooth and striated muscle; bone and bone marrow; skin; and tissues of the eye. The compositions are moreover useful in the treatment of non-cancer proliferative disorders. Non-cancer proliferative disorders are characterized by the uncontrolled growth of cells with a benign phenotype, meaning that the cells evade only the normal controls on growth, but cannot metastasize. Non-cancer proliferative disorders which may be treated with the present compounds include, but are not limited to, the following: hemangiomatosis in newborn; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Tumor cells treated with compositions of the invention accumulate in the G2/M phase of the cell cycle. As the cells exit the G2/M phase, they appear to undergo apoptosis. Treatment of normal cells with compositions of the present invention do not result in apoptosis.

EXAMPLES

Example I

Outline of Synthesis to Produce about 500 Grams of ON 01910.Na for Phase I Clinical Trials 1. (E)-2,4,6-Trimethoxystyryl-3'-nitro-4'-methoxy-benzylsulfone (2) (TNMBS)

One first condenses 2,4,6-trimethoxybenzaldehyde (TMBA) with 3-nitro-4-methoxybenzylsulfonylacetic acid (NBSA): To an appropriately sized glass reaction flask equipped with mechanical stirrer assembly, condenser, and gas inlet adapter for nitrogen charge 1.2 equivalents of 2,4,6-trimethoxybenzaldehyde. Begin agitation of the flask, and subsequently add a volume of toluene to the flask equal to 7 times the weight in grams of 3-nitro-4-methoxybenzylsulfonylacetic acid to be added. Charge the grams of acetic acid equivalent to 4 times the number of moles of NBSA multiplied by 102.09 g/mole. Finish raw material addition by adding 1.2 equivalents of NBSA. Begin condensation of the raw materials by heating the contents of the flask to reflux and maintain this reflux for a minimum of 5 hours until thin layer chromatography indicates that the TMBA is gone from the reaction mixture.

Reaction workup and product isolation is then completed: Cool the reaction mixture to about 65° C. and reduce the reaction volume to approximately 35% of the original volume with the aid of a rotary evaporator under reduced pressure. To the empty reaction flask, charge a volume of ethanol equivalent to 7 times the grams of NBSA used in the reaction. Again start the stirrer and slowly add the reduced volume of the reaction mixture to the ethanol. The intermediate (2) precipitates and is stirred for a minimum of 1 hour. The resulting solids are filtered and the filter cake is washed with an appropriate amount of ethanol. The wet filter cake is first dried under vacuum for a minimum of 8 hours at 25° C. followed by a subsequent drying period of at least 8 hours at 50° C.

Purification is accomplished in the following manner: To an appropriate sized flask equipped with agitator, condenser, and gas inlet adapter, one charges the crude product (2). A volume of ethyl acetate equivalent to 2 times the number of grams of NBSA used in the condensation reaction is subsequently added followed by a volume of acetonitrile equivalent to the number of grams of NBSA used in the condensation reaction. This mixture is stirred and heated to reflux for a minimum of 0.5 hours, and is subsequently cooled to ambient temperature for a minimum of 8 hours. The purified product is filtered, washed with ethyl acetate, and dried under vacuum at 50° C. for a minimum of 12 hours. The yield of intermediate TNMBS (2) is about 33%.

2. (E)-2,4,6-Trimethoxystyryl-3'-amino-4'-methoxy-benzylsulfone (3) (ON 01500)

Reactants are charged to the reaction vessel to effect reduction: An appropriately sized reaction flask equipped with a mechanical stirrer, gas inlet adapter and bubbler charge is used for the reduction reaction. One charges the reaction flask with 1 equivalent of TNMBS followed by a volume (ml) of acetic acid equivalent to 10 times the weight of TNMBS used in the reaction. Agitation is then started. A weight of zinc powder (4.5 equivalents) is slowly added to the reactor in small portions so that the temperature is maintained at 40° C.±5° C. The reaction is continued at this temperature until thin layer chromatography indicates that the TNMBS reactant has been consumed. The reaction is then terminated.

Product isolation follows completion of the reaction: One filters the reaction mixture through a celite cake to remove unreacted zinc powder. This filter cake is washed with volumes of acetic acid and ethyl acetate in order to rinse product from the cake. As a separate operation, the filter cake is quenched with water and disposed to hazardous waste. The filtrate is concentrated on a rotary evaporator at about 40° C. under vacuum to 30% of the original volume. Upon completion of this operation, a volume of water equivalent to 18 times the weight of TNMBS is added slowly to the reactor containing the concentrated filtrate. The reactor is cooled to about 10° C. in preparation for neutralization of the acetate salt of the intermediate (3). The reaction mixture is basified with 10M sodium hydroxide solution to a pH of 7.5 to 8.5 while maintaining a temperature at or below 20° C. The free amine precipitates during this procedure and the resulting mixture is stirred for a minimum of 3 hours to complete the precipitation. One filters the resulting solids and rinses the crude product with water followed by heptane. The solids are dried in a vacuum oven at 25° C. for at least 8 hours. This is followed by an extended drying period of 8 hours at 50° C.

Initial purification of the crude ON 01500 (3) is done using column chromatography with silica gel. Pack a large filter funnel with about 4000 grams of silica gel that has been slurried in dichloromethane. Weigh out a maximum of 850 grams of the crude ON 01500 and dissolve this in a minimum amount of dichloromethane. Carefully add the solution to the top of the silica gel column being careful not to disturb the silica gel bed. Cover with a piece of filter paper to prevent further disturbance. Elute the mixture of intermediate and impurities with dichloromethane and collect fractions consistent with the purity of the crude ON 01500. Monitor each fraction by thin layer chromatography for ON 01500 content. Subsequently elute the material on the column with 1% methanol in dichloromethane, followed by 2% methanol, 3% methanol, and 5% methanol until all materials have been removed from the column. Dispose of the spent silica gel to waste. The fractions containing only ON 01500 are combined and concentrated using a rotary evaporator at a bath temperature or 35° C.

The crude ON 01500 (3) is further purified as follows: With the use of a rotary evaporator flask to facilitate agitation, crude (3) is slurried with a volume of ethyl acetate equivalent to 3 times the original weight of TNMBS (2). At ambient pressure and under rotating conditions, heat the flask to reflux the solution and maintain this operation for a minimum of 0.5 hours. Allow the solution to cool to room temperature while stirring for a minimum of 8 hours. Filter the solids and rinse the filter cake with additional ethyl acetate in order to remove mother liquor from the cake. Dry the purified product in a vacuum oven at 50° C. under full vacuum for a minimum of 8 hours. The yield of ON 01500 is approximately 45% for this step of the process. The ON 01500 must have a purity of equal to or greater than 95% before proceeding to the next step.

3. Methyl-{N-[2-methoxy-5-methylene(2',4',6'-trimethoxystyrylsulfonyl)-phenyl]amino}acetate (4) (This is an Intermediate Ester to ON 01910 (Naming is Different))

To an appropriately sized reaction flask equipped with stirrer and addition funnel, one adds ON 01500 (3) via the addition funnel. Sodium acetate (3 equivalents per equivalent of the intermediate) is then added followed by an amount of ethanol in milliliters equivalent to six times the weight of ON 01500. The reactor is purged of air using UHP nitrogen. Methyl bromoacetate (1.5 equivalents per equivalent of ON 01500) is added to the reactor followed by sodium iodide (1.1 equivalents per equivalent of ON 01500. The agitated reaction mixture is heated to reflux for a minimum of 4 hours. Reaction completion is monitored by thin layer chromatography. Upon reaction completion, the mixture is cooled to 60° C. and the mixture is concentrated with a rotary evaporator at a bath temperature of 40° C. to approximately 30% of its original volume.

Isolation of the methyl ester (4) is then completed. The crude mixture is returned to the reaction flask and water (WFI grade) equivalent to 12 times the weight of ON 01500 (3) used in the reaction is slowly added. The resulting slurry is agitated for a minimum of 8 hours. The resulting solids are filtered through a tabletop filter and a Teflon filter cloth. The filter cake is washed with additional WFI and heptane. The isolated methyl ester (4) is placed on drying pans, covered with aluminum foil and is dried in a vacuum oven for at least 8 hours at 50° C. Yield of this step is 70%.

4. {N-[2-methoxy-5-methylene(2',4',6'-trimethoxy-styrylsulfonyl)phenyl]-amino}acetic acid Sodium salt (5) (ON 01910.Na)

To a properly sized reaction flask equipped with agitator, condenser, and nitrogen bubbler is charged an appropriate amount of the methyl ester (4) produced in the above step. A volume of ethanol (ml) equivalent to 6.6 times the weight of (4) is added to the flask. The flask is purged with nitrogen and water (WFI) equivalent to 3.3 times the weight of (4) is added. One adds 1.05 equivalents of sodium hydroxide pellets slowing to the reaction flask while it is being agitated. Agitation is continued for a minimum of 12 hours at ambient temperature. The completion of saponification is determined by the disappearance of (4) using thin layer chromatography. Once the reaction is complete, the mixture is filtered to remove miscellaneous solids and the filtrate is saved for isolation of the ON 01910.Na (5).

The product purification is carried out in the following manner. The filtrate from above is charged to a rotary evaporator, and the volume is reduced to approximately 20% of its original volume with the aid of a bath set at 40° C. The contents remaining are charged to an appropriately sized reaction flask equipped with an agitator assembly using water (WFI) equivalent to 3 times the weight of methyl ester (4) to dissolve the crude (5) and facilitate the transfer. Methyl t-butyl ether (ml) equivalent to 4 times the weight of (4) is added and the reaction mixture is vigorously stirred for 10 minutes. Agitation is stopped and the phases are allowed to partition for a minimum of 20 minutes. The organic phase is removed and the aqueous phase is further extracted twice in the manner described. The aqueous portion containing the product is filtered to remove miscellaneous solids and the solids are washed with additional WFI.

Product isolation follows the purification procedure. The filtered aqueous solution is transferred to a rotary evaporator with a bath temperature of 40° C. and the solvent is removed first at atmospheric pressure and then under high vacuum until the solids are dry and transferable (a minimum of 24 hours).

Purification/crystallization of the ON 01910.Na (5) is done in the following way. The crude solid (5) from above is transferred under a nitrogen purge to a reaction flask with an agitator assembly and nitrogen feed. The crude (5) is transferred to the flask and WFI (ml) is added equivalent to 2.5 times the crude weight of (5). The resulting solution is heated to about 43° C. and isopropanol is slowly added until the solution becomes cloudy and that cloudiness persists. (Approximately 12-15 ml/g of crude product is required). Continue agitation. If an oily residue is present, the solution may be filtered while hot and then promptly returned to the flask. Allow the solution to cool to ambient temperature while maintaining stirring for a minimum of 24 hours. One then filters the solids, washes them with isopropanol, and transfers them to drying pans for drying. The wet (5) is dried in a vacuum oven at ambient temperature for a minimum of 8 hours. Drying is continued at 70° C. for an additional 8 hours. The final drug substance (5) is cooled to 25° C. and an analytical sample is taken to determine the solvent content. Additional drying is done if the solvent content is above 0.5%. When (5) is completely dry, an analytical sample is again taken and the product is packaged. The yield is approximately 69% (if a second crop is taken from the mother liquor).

TABLE 2

Thin Layer Chromatography Process Control Points

| Reaction Step | TLC Conditions | Comments |
| --- | --- | --- |
| 1 | Silica gel plate spotted with starting materials and reaction mixture. Plate eluted with 20% heptane in ethyl acetate. Spots detected by UV light. | Reaction is complete when 2,4,6-trimethoxy-benzaldehyde starting material is no longer present in the reaction mixture. |
| 2 | Silica gel plate spotted with condensation product (2) and reaction mixture. Plate eluted with 20% ethyl acetate in dichloromethane. Spots detected by UV light. | Reaction is complete when none of the starting material (2) is visible. |
| 2 Column Chromatography | Silica gel plate spotted with column fraction and ON 01500. Plate eluted with 3:97:: methanol:dichloromethane. Spots detected by UV light. | Fractions containing only ON 01500 and no impurities were combined. |
| 2 Final Purification | Specifications established for the pure ON 01500. See table in following section. | |

TABLE 2-continued

Thin Layer Chromatography Process Control Points

| Reaction Step | TLC Conditions | Comments |
|---|---|---|
| 3 | Silica gel plate spotted with reaction mixture and ON 01500. Plate eluted with 25% heptane in ethyl acetate. Spots detected by UV light. | Reaction is complete when no ON 01500 is present in the reaction mixture. |
| 4 | Silica gel plate spotted with reaction mixture and the methyl ester (4). Plate eluted with ethyl acetate. Spots detected by UV light. | Reaction is complete when no methyl ester (4) is present in the reaction mixture. |

Example II

Formulation of ON 01910.Na Containing 50% PEG-400 in 0.016M Phosphate Buffer, pH 10.0

Materials
ON 01910.Na, Onconova Therapeutics, Inc.
Acetonitrile, ChromAR HPLC Grade (Lot no. 2856 X01B34) Mallinckrodt, Milwaukee, Wis.
Trifluoro Acetic Acid, 99%, Spectrochemical Grade Aldrich Chemicals, St. Louis, Mo.
Sodium Phosphate Dibasic, 12-Hydrate Crystals, USP Grade Mallinckrodt, Milwaukee, Wis.
Polyethylene Glycol 400, N.F. Grade, BASF Fine Chemicals, Mt. Olive, N.J.
85% O-Phosphoric Acid, A.R. Grade, Mallinckrodt, Milwaukee, Wis.

1. Preparation of 0.016 M Phosphate, pH 10:

Weigh approximately 2.6 grams of sodium phosphate tribasic, anhydrous. Transfer the material to a 1000 ml volumetric flask. Add approximately 750 mL water. Mix solution until all of the sodium phosphate tribasic has dissolved. Check pH. Adjust pH to 10.0±0.05 with either 0.1M phosphoric acid, or 0.1M NaOH. Q.S. solution to 1000 mL with water. Check final pH.

2. Preparation of 0.001 M Phosphoric Acid Solution:

Add 115 µL of 85% O-phosphoric acid to a 1000 mL volumetric flask. Q.S. solution to 1000 mL with water.

3. Preparation of 0.00025 M Phosphoric Acid Solution:

Transfer approximately 25 mL of 0.001 M phosphoric acid solution. Q.S. solution to 100 mL with water.

4. Preparation of 50% PEG-400 in 0.016 M Phosphate Buffer, pH 10.0:

The following is an example for a batch size of 1 mL. Transfer 0.5 mL of 0.016M phosphate buffer, pH 10.0. Record the weight. Transfer 0.5 mL of PEG-400. Record the weight. Mix solution.

Formulation of ON 01910.Na (NOVONEX™) containing 75 mg/mL drug, 50% PEG-400 in 0.016 M phosphate buffer, pH 10 provides for a stable formulation. Dilution of this product 1:7 with 0.00025 M phosphoric acid, for example, yields a product that has a pH of about 7.4 and osmolarity of approximately 300 mOsm/kg.

Example III

Stabilization of ON 01910.Na in an Aqueous Vehicle Suitable for Parenteral Administration A dramatic stabilization effect was observed by lowering the dielectric constant of the Formulation vehicle. A shelf stable formulation was developed based on PEG-400.

The effect of dielectric constant on the stabilization of ON 01910.Na, for example, was investigated, for example, by preparing formulations containing propylene glycol and PEG 400. The accelerated stability studies were preformed at 75 and 90° C. It was noticed that the stability of ON 01910.Na, for example, can be drastically improved by the addition of propylene glycol or PEG 400, for example, to an aqueous formulation. The following tables summarizes the results:

TABLE 3

% ON 01910.Na Remaining in formulations containing PEG at 75° C.

| % PEG | 0 D | 0.25 D | 2 D | 7 D | 14 D | 28 D |
|---|---|---|---|---|---|---|
| 0 | 100.00 | 86.47 | 11.20 | 0.47 | 0.47 | 0.02 |
| 25 | 100.00 | 98.12 | 66.89 | 42.13 | 32.03 | 29.80 |
| 50 | 100.00 | 100.32 | 94.76 | 86.06 | 75.80 | 68.73 |

The stability of ON 01910.Na was further improved by adjusting the pH of the aqueous medium above 8. The results of the effect of buffering at pH 10.0 is shown in Table 4.

TABLE 4

% ON 01910.Na Remaining in formulations containing PEG and buffer at 90° C.

| Composition | Control | After 72 hours |
|---|---|---|
| Water | 100.00 | 5.36 |
| PH 10 buffer | 100.00 | 50.18 |
| PEG:Water | 100.00 | 22.28 |
| PEG:Buffer | 100.00 | 94.22 |
| PG:Water | 100.00 | 15.79 |
| PG:Buffer | 100.00 | 79.62 |

The samples were evaluated by an HPLC assay utilizing a Phenomenex Luna C-18, 5 micron (4.6 mm×250 mm) reverse phase column at ambient conditions. The mobile phase consisted of 60%-0.1% Trifluoroacetic Acid in water: 40% Acetonitrile. The flow rate was set to 2.0 ml/minute and the eluant was monitored at 230 nm

Example IV

Stability Studies

ON 01910.Na Formulated in 100% PEG-400

Stability studies were carried out on 1.5 ml dosage amounts of the formulated ON 01910.Na in 100% PEG-400 in sealed 5 mL glass vials for a period of 12 weeks.

TABLE 5

Stability of 100% PEG-400 ON 01910.Na Formulation as Function of Time & Temperature Assay, % wt/wt

| Storage Condition | Timepoint (weeks) | | | | | |
|---|---|---|---|---|---|---|
| | Initial* | 1 week | 2 week | 4 week | 8 week | 12 week |
| 5° C. | 6.360 | — | — | — | — | 6.341 |
| 25° C./60% RH | — | 6.342 | 6.253 | 6.336 | 6.447 | 6.180 |
| 40° C./75% RH | — | 6.392 | 6.238 | 6.289 | 6.323 | 6.129 |
| 75° C. | — | 6.070 | 5.759 | 5.428 | 5.234 | 4.890 |

Example V

Long term Stability Studies of ON 01910.Na Formulated in 100% PEG-400 for Clinical Use Indicate that ON 01910.Na is Extremely Stable in the Current Formulation, and is Expected That There Will not be any Significant Degradation Over a Two Year Period ON 01910.Na IV solution was manufactured at a concentration of 75 mg/mL in 100% PEG-400. The finished product consisted of 3 mL of drug product aseptically filled into presterilized 5 mL vials. The manufacturing was in compliance with current Good Manufacturing Practices regulations.

TABLE 6

Testing Frequency & Storage Conditions:

| Storage Conditions | Scope of Stability Study Months for Study | | | | | | |
|---|---|---|---|---|---|---|---|
| | 0 | 3 | 6 | 9 | 12 | 18 | 24 |
| 5° C. ± 3° C. (Long Term) | + | + | + | + | + | + | + |
| 5° C. ± 3° C. | + | | + | | + | | + |
| 25° C. ± 2° C. 60% RH ± 5% RH (Accelerated) | (a) | + | + | + | + | + | |

Visual Inspection
(a) The zero-time data point is the same as the release data generated from the manufactured clinical lot.

Analytical Methods:

(a) HPLC—Chromatography is performed using a Phenomenex Luna C-18 (2), 5 micron (4.6 mm×250 mm, PN 00G-4252-E0) column at ambient conditions. The mobile phase used is 60%-0.1% trifluoroacetic acid in water; 40% acetonitrile. The flow rate is set at 2.0 ml/min Injection volume is 50 μL. Detection is accomplished by means of a UV/VIS detector at 230, 254, and 320 nm. Instrument control and data acquisition is facilitated using a Waters Millennium (V 2.15) software package. The external calibration is obtained using ON 01910.Na standard solutions prepared in 50:50 acetonitrile:water. This analytical method was validated.

TABLE 7

HPLC Stability Data for the ON 01910.Na Stability Samples

| | 5° C. Storage | | 25° C. Storage | |
|---|---|---|---|---|
| Day | Assay (mg/mL) | Average Assay (mg/mL) [% RSD] | Assay (mg/mL) | Average Assay (mg/mL) [% RSD] |
| 0 | 72.81 | | 72.81 | |
| 0 | 78.26 | 76.49 [4.16] | 78.26 | 76.49 [4.16] |
| 0 | 78.39 | | 78.39 | |
| 30 | 70.17 | | 77.77 | |
| 30 | 75.86 | 72.88 [3.91] | 78.14 | 78.28 [0.75] |
| 30 | 72.63 | | 78.92 | |
| 90 | 76.35 | | 71.74 | |
| 90 | 69.57 | 71.24 [6.33] | 70.20 | 69.97 [2.72] |
| 90 | 67.81 | | 67.96 | |
| 180* | 74.52 | | 73.34 | |
| 180* | 75.94 | 75.02 [1.1] | 70.40 | 71.38 [2.4] |
| 180* | 74.61 | | 70.39 | |
| 270* | 76.72 | | 74.94 | |
| 270* | 77.12 | 77.12 [0.52] | 74.12 | 74.29 [0.79] |
| 270* | 77.51 | | 73.81 | |
| 365* | 77.75 | | 77.88 | |
| 365* | 79.53 | 78.64 (1.13) | 77.47 | 77.56 (0.36) |
| 365* | 78.64 | | 77.34 | |

*These data were generated using weighed samples instead of pipetted volumes of the formulation.

Example VI

This example summarizes the results of a compatibility study of ON 01910.Na drug product (75 mg/ml in PEG-400) in IV Infusion Bags and Sets containing 0.45% NaCl and 0.9% NaCl solutions. The study consisted of preparing solutions of 80 mg of the ON 01910.Na in 250 ml 0.9% NaCl, and 800 mg of ON01910.Na in 250 ml 0.45% NaCl, and storing them in IV infusion bags for over 24 hours to determine if there is any product loss or instability. The solutions were also passed through infusion sets at a rate of approximately 2 ml per minute for 120 minutes and monitored for product loss or instability.

The samples were analyzed by HPLC for Assay, % Recovery, and Impurities. Appearance, Osmolarity, and pH of the solutions were also monitored throughout the study.

| Material | Vendor | Lot # |
|---|---|---|
| ON 01910.Na | ChemPacific | |
| Polyethylene Glycol 400 (PEG-400) | J. T. Baker | Y111608 |
| 0.9% Sodium Chloride Injection USP (250 ml infusion bag) | Baxter International | C605089 (exp. May 2005) |
| Low Sorbing Sterile Injection Set | Alaris Medical Systems | 309276 (exp. September 2006) |
| Sterile Water for Injection USP | | C614388 (exp. May 2005) |

Preparation of 75 mg/ml ON 01910.Na in 100% PEG-400 (Corrected for Moisture)

54.6955 g PEG-400

3.892 g ON01910.Na (6.0% moisture—correction factor 0.94)

The samples for the stability study were prepared by slowly adding the ON01910.Na to the PEG-400 with stirring, and mixing until the solution became a clear yellow solution.

80 mg ON 01910.Na in 0.9% Sodium Chloride

Each infusion bag was prepared by transferring 1.1 ml ON01910.Na drug product (75 mg/ml in PEG-400) solution, using a 3 ml syringe, via port into an infusion bag containing 250 ml of 0.9% NaCl. The infusion bag was then shaken. The syringe was rinsed with IV fluid, and the fluid returned to the bag.

800 mg ON01910.Na in 0.45% Sodium Chloride

Each infusion bag was prepared by first removing 125 ml of solution from a 250 ml infusion bag containing 0.9% Sodium Chloride and adding 125 ml of Sterile Water for Injection to the bag. 10.7 ml of ON01910.Na drug product (75 mg/ml in PEG-400) was transferred, using a 20 ml syringe via port into an infusion bag containing 250 ml of 0.45% NaCl. The bag was then shaken. The syringe was rinsed with IV fluid, and the fluid returned to the bag.

Infusion Bag Compatibility Study

Two infusion bags containing 80 mg ON01910.Na in 250 ml 0.9% NaCl, and two bags containing 800 mg ON01910.Na in 250 ml 0.45% NaCl, were prepared as described above.

Five ml of solution were removed from each bag for analysis at the following time points: T=0, 1 hr, 2 hr, 4 hr, 8 hr, and 24.5 hr. Appearance, Assay, % Impurities, % Recovery, Osmolarity, and pH were analyzed at each time points.

Infusion Set Compatibility Study

Two infusion bags containing 80 mg ON01910.Na in 250 ml 0.9% NaCl, and two bags containing 800 mg ON01910.Na in 250 ml 0.45% NaCl, were prepared as described above. An infusion set and in-line filter were attached to each bag and the flow rate set to approximately 2 ml per minute.

Six samples per infusion set were collected for analysis at the following intervals: first, second, and third 5 ml portions, then 5 ml portions at 30, 60, and 120 min Appearance, Assay, % Impurities, % Recovery, Osmolarity, and pH were performed for each portion.

HPLC Conditions

Column: Phenomenex LUNA C18, 5 μm, 250×4.6 mm
Column Temp: 40° C.
Flow Rate: 1.0 ml/min
Run Time: 45 min
Injection Size: 10 μL
Detection: UV at 215 nm
Mobile phase A: Phosphate buffer pH 8 (0.01M $KH_2PO_4$)
Mobile phase B: Acetonitrile

TABLE 8

| Gradient | |
|---|---|
| Time, minutes | % Mobile phase B |
| 0 | 25 |
| 5 | 25 |
| 12 | 35 |

TABLE 8-continued

| Gradient | |
|---|---|
| Time, minutes | % Mobile phase B |
| 18 | 35 |
| 30 | 55 |
| 35 | 55 |
| 36 | 25 |
| 45 | 25 |

Mobile Phase and Diluent Preparation

Mobile Phase Mobile Phase A was prepared by mixing 4.083 g of $KH_2PO_4$ with 3 liters deionized water, and adjusting to pH 8 with 10N KOH.

Diluent: Mobile Phase A and acetonitrile were mixed 5:25 v/v.

Standards Preparation

A stock solution containing 3194 μg/ml ON 01910.Na was prepared in diluent. The stock solution was diluted to working standard solutions following the dilution scheme listed in Table 9. The first three standards were used for the standard curve to quantify the low dose experiment (80 mg of ON 01910.Na per 251.1 ml resulting in 329 m/ml concentration) and the last three and stock standards were used for the standard curve to quantify the high dose (800 mg ON 01910.Na per 260.7 ml resulting in 3078 m/ml concentration).

TABLE 9

Standard Preparation of ON01910.Na Solutions

| Standard | Volume (ml) Transferred | Final Volume (ml) | Concentration (μg/ml) |
|---|---|---|---|
| STD 1 | 0.50 | 10.0 | 160 |
| STD 2 | 0.75 | 10.0 | 240 |
| STD 3 | 1.00 | 10.0 | 319 |
| STD 4 | 0.50 | 1.0 | 1597 |
| STD 5 | 0.75 | 1.0 | 2396 |
| STD 6 | 0.90 | 1.0 | 2875 |

Results

Results are shown in Tables 10-13. % Recovery is the percentage of drug substance as compared to the calculated amount, while % $T_0$ is defined as the percentage of drug substance as compared to drug substance at the initial timepoint. Impurities are peaks other than the ON 01910.Na main peak.

TABLE 10

Stability Results of 80 mg in 250 ml 0.9% Sodium Chloride IV Bags

| | | Initial | 1 hour | 2 hours | 4 hours | 8 hours | 24.5 hours |
|---|---|---|---|---|---|---|---|
| Appearance | 1 | Slight yellow solution | Slight yellow solution | Slight yellow solution | Slight yellow solution | Slight yellow solution | Slight yellow solution |
| | 2 | Slight yellow solution | Slight yellow solution | Slight yellow solution | Slight yellow solution | Slight yellow solution | Slight yellow solution |
| pH | 1 | 6.56 | 6.61 | 6.74 | 6.58 | 6.50 | 6.60 |
| | 2 | 6.60 | 6.41 | 6.78 | 6.72 | 6.45 | 6.34 |
| Osmolarity mOsm/kg | 1 | 299 | 299 | 299 | 300 | 299 | 299 |
| | 2 | 300 | 300 | 300 | 301 | 299 | 300 |
| Assay ON01910.Na μg/ml (% $T_0$) | 1 | 320.1 | 319.7 (99.9%) | 319.7 (99.9%) | 319.0 (99.6%) | 318.5 (99.5%) | 314.5 (98.2%) |
| | 2 | 329.3 | 329.4 (100.0%) | 328.9 (99.9%) | 329.0 (99.9%) | 327.1 (99.4%) | 324.0 (98.4%) |
| % Recovery | 1 | 97.42 | 97.31 | 97.31 | 97.07 | 96.92 | 95.71 |
| | 2 | 100.21 | 100.26 | 100.10 | 100.13 | 99.56 | 98.62 |
| Impurities μg/ml (% $T_0$) | 1 | 5.62 | 7.38 (131.4%) | 7.10 (126.4%) | 6.32 (112.5%) | 6.30 (112.1%) | 5.86 (104.3%) |
| | 2 | 7.50 | 7.19 (95.9%) | 7.00 (93.3%) | 6.85 (91.4%) | 6.71 (89.6%) | 5.51 (73.5%) |

TABLE 11

Stability Results of 800 mg in 250 ml 0.45% Sodium Chloride IV Bags

|  |  | Initial | 1 hour | 2 hours | 4 hours | 8 hours | 24.5 hours |
|---|---|---|---|---|---|---|---|
| Appearance | 1 | Yellow Solution | Yellow Solution | Yellow Solution | Yellow Solution | Yellow Solution | Yellow Solution |
|  | 2 | Yellow Solution | Yellow Solution | Yellow Solution | Yellow Solution | Yellow Solution | Yellow Solution |
| pH | 1 | 7.02 | 6.98 | 6.89 | 7.01 | 6.82 | 6.85 |
|  | 2 | 6.94 | 6.92 | 6.96 | 6.87 | 6.75 | 6.63 |
| Osmolarity mOsm/kg | 1 | 296 | 297 | 297 | 300 | 296 | 297 |
|  | 2 | 296 | 297 | 298 | 301 | 297 | 296 |
| Assay ON01910.Na µg/ml (% $T_0$) | 1 | 2693.5 | 2674.0 (99.3%) | 2683.6 (99.6%) | 2659.0 (98.7%) | 2666.0 (99.0%) | 2624.5 (97.4%) |
|  | 2 | 2665.6 | 2665.7 (100.0%) | 2663.1 (99.9%) | 2689.3 (100.9%) | 2642.4 (99.1%) | 2616.0 (98.1%) |
| % Recovery | 1 | 87.49 | 86.86 | 87.17 | 86.37 | 86.60 | 85.25 |
|  | 2 | 86.59 | 86.59 | 86.51 | 87.36 | 85.84 | 84.98 |
| Impurities µg/ml (% $T_0$) | 1 | 9.98 | 10.13 (101.5%) | 10.05 (100.7%) | 9.69 (97.1%) | 9.36 (93.8%) | 9.75 (97.7%) |
|  | 2 | 10.74 | 10.49 (97.6%) | 10.60 (98.7%) | 9.57 (89.1%) | 9.83 (91.6%) | 10.00 (93.1%) |

TABLE 12

Stability Results of 80 mg in 0.9% Sodium Chloride Infusion Sets

|  |  | $1^{st}$ 5 ml | $2^{nd}$ 5 ml | $3^{rd}$ 5 ml | 30 min | 60 min | 120 min |
|---|---|---|---|---|---|---|---|
| Appearance | 1 | Slight yellow solution | Slight yellow solution | Slight yellow solution | Slight yellow solution | Slight yellow solution | Slight yellow solution |
|  | 2 | Slight yellow solution | Slight yellow solution | Slight yellow solution | Slight yellow solution | Slight yellow solution | Slight yellow solution |
| pH | 1 | 6.90 | 6.86 | 6.59 | 6.76 | 6.82 | 6.56 |
|  | 2 | 6.64 | 6.68 | 6.67 | 6.57 | 6.74 | 6.74 |
| Osmolarity mOsm/kg | 1 | 301 | 299 | 300 | 301 | 301 | 301 |
|  | 2 | 300 | 300 | 300 | 303 | 301 | 301 |
| Assay ON01910.Na µg/ml (% $T_0$) | 1 | 321.2 | 325.0 (101.2%) | 324.5 (101.0%) | 325.1 (101.2%) | 324.9 (101.2%) | 324.4 (101.0%) |
|  | 2 | 314.1 | 321.1 (102.2%) | 321.6 (102.4%) | 321.9 (102.5%) | 322.7 (102.7%) | 322.0 (102.5%) |
| % Recovery | 1 | 97.75 | 98.92 | 98.76 | 98.93 | 98.88 | 98.72 |
|  | 2 | 95.60 | 97.72 | 97.88 | 97.96 | 98.22 | 97.99 |
| Impurities µg/ml (% $T_0$) | 1 | 4.94 | 5.17 (104.7%) | 5.18 (104.9%) | 5.25 (106.3%) | 5.20 (105.2%) | 4.83 (97.8%) |
|  | 2 | 5.14 | 5.08 (98.9%) | 5.43 (105.6%) | 5.44 (105.9%) | 5.34 (103.9%) | 5.17 (100.6%) |

TABLE 13

Stability Results of 800 mg in 0.45% Sodium Chloride Infusion Sets

|  |  | $1^{st}$ 5 ml | $2^{nd}$ 5 ml | $3^{rd}$ 5 ml | 30 min | 60 min | 120 min |
|---|---|---|---|---|---|---|---|
| Appearance | 1 | Yellow solution | Yellow solution | Yellow solution | Yellow solution | Yellow solution | Yellow solution |
|  | 2 | Yellow solution | Yellow solution | Yellow solution | Yellow solution | Yellow solution | Yellow solution |
| pH | 1 | 6.96 | 7.00 | 6.95 | 6.99 | 6.96 | 7.04 |
|  | 2 | 6.99 | 6.98 | 7.00 | 6.94 | 7.02 | 6.81 |
| Osmolarity mOsm/kg | 1 | 302 | 303 | 304 | 303 | 300 | 299 |
|  | 2 | 304 | 301 | 305 | 304 | 303 | 301 |
| Assay ON01910.Na µg/ml (% $T_0$) | 1 | 2710.3 | 2714.2 (100.1%) | 2719.9 (100.4%) | 2746.2 (101.3%) | 2728.0 (100.7%) | 2709.9 (100.0%) |
|  | 2 | 2714.3 | 2728.4 (100.5%) | 2707.1 (99.7%) | 2767.5 (102.0%) | 2724.4 (100.4%) | 2708.4 (99.8%) |
| % Recovery | 1 | 88.04 | 88.17 | 88.35 | 89.21 | 88.62 | 88.03 |
|  | 2 | 88.17 | 88.63 | 87.94 | 89.90 | 88.50 | 87.98 |
| Impurities µg/ml (% $T_0$) | 1 | 10.02 | 10.18 (101.6%) | 10.14 (101.2%) | 9.97 (99.5%) | 10.23 (102.1%) | 10.36 (103.4%) |
|  | 2 | 9.94 | 9.99 (100.5%) | 10.01 (100.8%) | 9.77 (98.3%) | 10.12 (101.8%) | 10.45 (105.2%) |

The formulation of 75 mg/ml ON 01910.Na in PEG-400 is stable over 24 hours in IV infusion bags containing 0.45% NaCl and 0.9% NaCl solutions.

Example VII

Example Reaction Scheme (ON 01910.Na Clinical Material)

Figure 2:
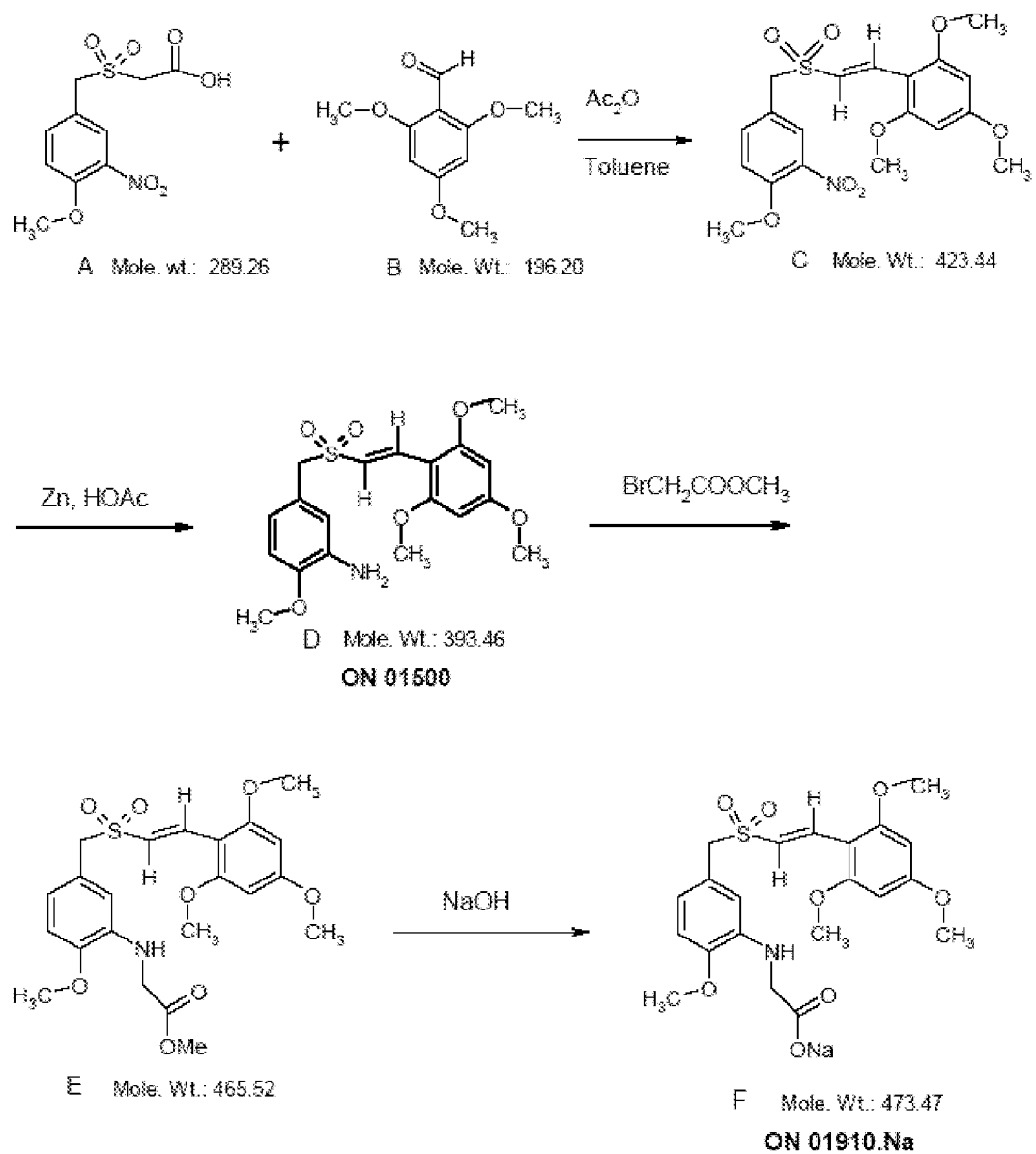
FIG. 2 displays a flowchart outlining a further method of synthesis of the sodium salt of (E)-2,4,6-trimethoxystyryl-3-carboxymethylamino-4-methoxybenzylsulfone (ON 01910.Na).

Synthesis of the clinical trial quantity of ON 01910.Na carried out by ChemPacific Co., USA, is described. The synthesis started with purchased 2,4,6,-trimethoxybenzaldehyde (Hunan Xinyu, Changsha, China) and 3-nitro-4-methoxybenzylsulfonylacetic acid (ChemPacific Co., Hangzhou, China). This latter starting material was qualified via ChemPacific Co., USA to be certain of quality. The synthesis was done under cGMP conditions. See, FIG. 2.

1. (E)-2,4,6-Trimethoxystyryl-3'-nitro-4'-methoxybenzylsulfone (Compound C)

A gentle stream of nitrogen was allowed to pass through a 22-liter glass reactor that was equipped with a mechanical stirrer assembly, a condenser, a thermometer, and a gas inlet adaptor. A quantity of 3-nitro-4-methoxybenzylsulfonylacetic acid (Compound A, 1775 g, 6.14 atom molecule) and a quantity of 2,4,6-trimethoxybenzaldehyde (Compound B, 1200 g, 6.12 atom molecule) were both charged to the reactor. Agitation was started as both 12 L of anhydrous toluene and 2448 g of acetic anhydride were charged slowly to the reactor. The suspension was stirred and heated to reflux for a minimum of 4 hours until thin layer chromatographic test indicated the total consumption of compound B was reached.

The reaction mixture was cooled and filtered through a Buchner funnel. The filter cake was washed with 3 liter of hexane and subsequently dried under house vacuum (20 mmHg) for a minimum of 8 hours at 25° C., to yield first crop of product. The filtrate and washings were combined and further concentrated using a rotary evaporator (water bath was kept below 70 C and vacuum was measured at 20 mmHg) to give a product which then was taken into 3 liters of ethyl acetate and left standing at 0 C overnight. A solid was formed and the second crop of the product was collected by filtration. The filter cake was further rinsed with hexane (1 L) then dried under vacuum for at least 8 hours at ambient temperature. Total combined product Compound C weighed 1350 g with a yield of 52%.

2. (E)-2,4,6-Trimethoxystyryl-3'-amino-4'-methoxybenzylsulfone (Compound D) (ON 01500)

To a 22-liter glass reactor equipped with a mechanical stirrer, a thermometer, and a gas inlet adapter for protective nitrogen were introduced Compound C (925 g, 2.18 Mole) and acetic acid (10 L). The suspension was cooled below ambient temperature. Zinc powder (925 g, 14.23 Mole) was slowly added to the reactor in small portions so that the temperature is maintained under ambient temperature ° C. The reaction was continued at this temperature until thin layer chromatography indicated that Compound C was totally consumed.

The crude mixture was filtered through a pad of celite and the filter cake was washed with 4 liters of acetic acid. The combined filtrate and washings were mixed with cold water. The pH was brought to 3-8 with 25% of sodium hydroxide while maintaining a temperature at or below room temperature. The resulting precipitate stirred for a minimum of 3 hours before it was filtered. The filter cake was rinsed with hexane and the solid dried under a house vacuum for at least 8 hours. Compound D in its crude form weighed 725 g, 87% yield.

The crude product (725 g, dissolved in dichloromethane) was first loaded to a column of silica gel pre-packed with 4000 g of silica gel powder. A filter paper was used to cover the silica gel bed to prevent disturbance cause by the addition of eluent. Thus dichloromethane was added slowly and fractions were collected. The TLC technique was used to monitor the content of Compound D in the fractions. Subsequent elution with 1%, 2%, 3% and 5% methanol in dichloromethane assured sufficient collection of the desired compound. The fractions containing Compound D were pooled and solvent evaporated using rotary evaporator. The water bath should not go beyond 35° C.

The crude ON 01500 (Compound D) is further purified as follows: With the use of a rotary evaporator flask to facilitate agitation, the crude (Compound D) is slurried with a volume of ethyl acetate equivalent to 3 times the original weight of Compound C. At ambient pressure and under rotating conditions, heat the flask to reflux the solution and maintain this operation for a minimum of 0.5 h. Allow the solution to cool to room temperature while stirring for a minimum of 8 hours. Filter the solids and rinse the filter cake with additional ethyl acetate in order to remove mother liquor vacuum for a minimum of 8 hours. The yield of ON 01500 is approximately 45% for this step of the process. The ON 1500 must have a purity of equal to or greater than 95% before proceeding to the next step.

The purity of the product can be still further improved by using the following procedure:
Take 725 g of Compound D into 2 L of dichloromethane. Add 4 L of ethyl acetate. Concentrate the solvent to obtain a yellow precipitate. The resulting solid is further treated with either hot ethanol or isopropanol. Cooling the mixture to room temperature and filtering gave a light colored product (450 g, 52%) with purity more than 98.5%.

3. (E)-2,4,6-Trimethoxystyryl 3-(carbomethoxymethylamino)-4-methoxybenzyl-sulfone (Compound E)

To a solution of Compound D (ON-1500, 733 g, 1.86 mol) methanol (12 L) was added sodium acetate (751 g, 8.24 mol) and ethyl 2-bromoacetate (70 mL, 7.3 mol). The mixture was refluxed overnight and the reaction was monitored by thin layer chromatography (dichloromethane: EtOAc, 4:1). Upon completion of the reaction, the mixture was concentrated under reduced pressure and the residue was treated with hexane and ethyl acetate. An off-white solid product was collected by filtration to give Compound E (823 g, 95%).

4. (E)-2,4,6-Trimethoxystyryl 3-[(carboxymethyl)amino]-4-methoxybenzyl-sulfone, Sodium Salt (Compound F) this is the Drug Substance, on 01910.Na Compound E (823 g, 1.77 mol) was treated with 20% sodium hydroxide (1840 mL) in methanol (15 L) at ambient temperature and the reaction was monitored by thin layer chromatography (chloroform:methanol:acetic acid=15:1:1). Upon the completion of the reaction, the mixture was concentrated to give a lightly colored crystal, which was filtered. The filter cake was treated with ethanol, THF, and diethyl-ether, and the product was subsequently dried over house vacuum to give compound F as an off-white solid: weight, 550 g; 65% and HPLC purity >98%.

Example VIII

ON.1910.Na Exemplary Formulation and Stability

Phosphate buffer, pH 10.0-50%
PEG 400-50%

Mix phosphate buffer and PEG 400 in a 1:1 ratio. Add enough ON.01910.Na to prepare a solution at a concentration of 75 mg/ml.

TABLE 14

ACCELERATED 50% PEG (40° C. & 75% RH)

| Number of Days | Concentration found (mg/ml) | Colour | pH |
|---|---|---|---|
| 0 | 71.4517 | Yellow | 10.68 |
| 15 | 71.523 | Yellow | 10.79 |
| 45 | 71.175 | Yellow | 10.14 |
| 60 | 71.322 | Yellow | 11.38 |
| 90 | 71.949 | Yellow | 10.7 |
| 120 | 71.697 | Yellow | 10.54 |
| 150 | 71.12 | Yellow | 10.45 |
| 180 | 70.824 | Yellow | 10.53 |

Solution concentration: 75 mg/ml

TABLE 15

LONGTERM 50% PEG (25° C. & 60% RH)

| Number of Days | Concentration found (mg/ml) | Colour | pH |
|---|---|---|---|
| 0 | 71.4517 | Yellow | 10.68 |
| 15 | 72.402 | Yellow | 10.65 |
| 45 | 71.66 | Yellow | 10.39 |
| 60 | 71.78 | Yellow | 10.81 |
| 90 | 72.51 | Yellow | 10.84 |
| 120 | 70.993 | Yellow | 10.46 |
| 150 | 72.38 | Yellow | 11.03 |
| 180 | 71.421 | Yellow | 10.95 |

Solution concentration: 75 mg/ml

Example IX

ON.1910.Na Exemplary Formulation and Stability

TABLE 16

LONGTERM 50% PEG (25° C. & 60% RH)

| Number of Days | Concentration found (mg/ml) | Colour | pH |
|---|---|---|---|
| 0 | 71.4517 | Yellow | 10.68 |
| 15 | 72.402 | Yellow | 10.65 |
| 45 | 71.66 | Yellow | 10.39 |
| 60 | 71.78 | Yellow | 10.81 |
| 90 | 72.51 | Yellow | 10.84 |
| 120 | 70.993 | Yellow | 10.46 |
| 150 | 72.38 | Yellow | 11.03 |
| 180 | 71.421 | Yellow | 10.95 |
| 270 | 71.64 | Yellow | 11.22 |

Solution concentration: 75 mg/ml

For comparison purposes the 25% PEG based formulation is not so stable:

TABLE 17

LONGTERM 25% PEG (25° C. & 60% RH)

| Number of Days | Concentration found (mg/ml) | Colour | pH |
|---|---|---|---|
| 0 | 71.432 | Yellow | 10.97 |
| 15 | 72.314 | Yellow | 9.88 |
| 45 | 72.186 | Yellow | 9.8 |
| 60 | 72.5 | Yellow | 10.29 |
| 90 | 70.703 | Yellow | 9.94 |
| 120 | 1.491 | Yellow | 10.27 |
| 150 | 72.52 | Yellow | 9.79 |
| 180 | 70.4745 | Turbid Yellow | 9.72 |
| 270 | 66.37 | Turbid Yellow | 9.75 |

Solution concentration: 75 mg/ml

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described compositions and modes for carrying out the invention which are obvious to those skilled in the art or related fields are intended to be within the scope of the following claims.

What is claimed is:

1. An aqueous composition for parenteral administration comprising an effective amount of a sodium salt of (E)-2,4,6-trimethoxystyryl-3-carboxymethylamino-4-methoxybenzylsulfone (ON 01910.Na) and 25% to 47.5% by weight of a polyethylene glycol comprising PEG 300, PEG 400, PEG 600, or PEG 800, and a buffer, wherein the composition is in a pH range of about 8 to about 14, and wherein the buffer is a phosphate buffer and osmolarity of the aqueous composition is 300 mOsm/kg.

2. The composition of claim 1 comprising 30% by weight of said polyethylene glycol.

3. The composition of claim 1 comprising 40% by weight of said polyethylene glycol.

4. The composition of claim 1 comprising 45% by weight of said polyethylene glycol.

5. The composition of claim 1 which has a pH within a range of about 9 to about 11.5.

6. The composition of claim 1 which comprises PEG 400.

7. The composition of claim 1 which comprises about 10 mg/ml to about 200 mg/ml of the sodium salt of (E)-2,4,6-trimethoxystyryl-3-carboxymethylamino-4-methoxybenzylsulfone (ON 01910.Na).

8. The composition of claim 7 which comprises about 40 mg/ml to about 120 mg/ml of the sodium salt of (E)-2,4,6-trimethoxystyryl-3-carboxymethylamino-4-methoxybenzylsulfone (ON 01910.Na).

9. The composition of claim 8 which comprises about 75 mg/ml of the sodium salt of (E)-2,4,6-trimethoxystyryl-3-carboxymethylamino-4-methoxybenzylsulfone (ON 01910.Na).

10. A composition for prevention or treatment of a pathophysiological condition in a mammal consisting essentially of about 4% to about 10% by weight of sodium salt of (E)-2,4,6-trimethoxystyryl-3-carboxymethylamino-4-methoxybenzylsulfone (ON 01910.Na) and 25% to 47.5% by weight of a polyethylene glycol comprising PEG 300, PEG 400, PEG 600, or PEG 800, and a buffer, wherein the composition is in a pH range of about 8 to about 14, and wherein the buffer is a phosphate buffer and osmolarity of the aqueous composition is 300 mOsm/kg.

11. The composition of claim 10 which comprises about 25 mg to about 125 mg of the sodium salt of (E)-2,4,6-trimethoxystyryl-3-carboxymethylamino-4-methoxybenzylsulfone (ON 01910.Na) per ml in about 30% to 35% PEG-400.

12. The composition of claim 10 comprising about 75 mg of the sodium salt of (E)-2,4,6-trimethoxystyryl-3-carboxymethylamino-4-methoxybenzylsulfone (ON 01910.Na) per ml in about 40% PEG-400.

* * * * *